United States Patent
Hou et al.

(10) Patent No.: US 9,610,448 B2
(45) Date of Patent: Apr. 4, 2017

(54) SYSTEM AND METHOD TO CONTROL A NON-PARESTHESIA STIMULATION BASED ON SENSORY ACTION POTENTIALS

(71) Applicant: PACESETTER, INC., Sylmar, CA (US)

(72) Inventors: Wenbo Hou, Santa Clarita, CA (US); Melanie Goodman Keiser, McKinney, TX (US); Xiaoyi Min, Camarillo, CA (US); Bruce A. Morley, Garland, TX (US)

(73) Assignee: Pacesetter, Inc., Sylmar, CA (US)

( * ) Notice: Subject to any disclaimer, the term of this patent is extended or adjusted under 35 U.S.C. 154(b) by 106 days.

(21) Appl. No.: 14/539,802

(22) Filed: Nov. 12, 2014

(65) Prior Publication Data
US 2016/0129272 A1 May 12, 2016

(51) Int. Cl.
*A61N 1/00* (2006.01)
*A61N 1/372* (2006.01)
*A61N 1/36* (2006.01)

(52) U.S. Cl.
CPC ..... *A61N 1/37241* (2013.01); *A61N 1/36071* (2013.01); *A61N 1/36135* (2013.01); *A61N 1/37264* (2013.01)

(58) Field of Classification Search
CPC .............. A61N 1/37241; A61N 1/3606; A61N 1/37264; A61N 1/36128; A61N 1/36132; A61N 1/36135; A61N 1/36164; A61N 1/3605
See application file for complete search history.

(56) References Cited

U.S. PATENT DOCUMENTS

| | | |
|---|---|---|
| 7,212,110 B1 | 5/2007 | Martin et al. |
| 7,228,179 B2 | 6/2007 | Campen et al. |
| 7,571,007 B2 | 8/2009 | Erickson et al. |
| 2006/0170486 A1 | 8/2006 | Tranchina et al. |
| 2009/0326608 A1 | 12/2009 | Huynh et al. |
| 2011/0313483 A1* | 12/2011 | Hincapie Ordonez ............ A61B 5/04001 607/17 |

FOREIGN PATENT DOCUMENTS

WO    0193953 A1    12/2001

OTHER PUBLICATIONS

Betts, R.P. et al, "Nerve fibre velocity and refractory period distributions in nerve trunks," Journal of Neurology, Neurosurgery, and Psychiatry. 1976;39:694-700.
Parker, John L et al., "Compound action potentials recorded in the human spinal cord during neurostimulation for pain relief," PAIN. 2012;153:593-601.

* cited by examiner

*Primary Examiner* — Mallika D Fairchild

(57) ABSTRACT

A system and method for controlling non-paresthesia stimulation of nervous tissue of a patient. The method delivers a non-paresthesia stimulation waveform, senses sensory action potential (SAP) signals from the nervous tissue of interest, and analyzes the SAP signals to obtain SAP activity data for at least one of an SAP C-fiber component or an SAP A-delta fiber component. The method determines whether the SAP activity data satisfies a criteria of interest and adjusts at least one of the therapy parameters to change the non-paresthesia stimulation waveform when the SAP activity data does not satisfy the criteria of interest.

14 Claims, 10 Drawing Sheets

VISUAL ANALOG
SCALE

SYSTEM AND METHOD TO CONTROL A NON-PARESTHESIA STIMULATION BASED ON SENSORY ACTION POTENTIALS

FIELD OF THE INVENTION

Embodiments of the present disclosure generally relate to neurostimulation (NS), and more particularly to controlling non-paresthesia stimulation signals in connection with pain relief.

BACKGROUND OF THE INVENTION

Spinal cord stimulation (SCS) is used to treat a wide range of chronic neuropathic pain conditions by delivering electrical stimulation to select portions of the spinal cord. In the past, SCS therapy has been proposed in which a tonic therapy is defined by single pulses have a select pulse width, frequency and intensity. By way of example, tonic therapies have been proposed to manage cervical and lumbar pain. The pulse width, frequency and intensity may be changed, along with electrode configuration and placement on the spinal column in connection with pain relief for individual patients.

NS systems are devices that generate electrical pulses and deliver the pulses to nervous tissue to treat a variety of disorders. For example, spinal cord stimulation has been used to treat chronic and intractable pain. Another example is deep brain stimulation, which has been used to treat movement disorders such as Parkinson's disease and affective disorders such as depression. While a precise understanding of the interaction between the applied electrical energy and the nervous tissue is not fully appreciated, it is known that application of electrical pulses to certain regions or areas of nervous tissue can effectively reduce the number of pain signals that reach the brain. For example, applying electrical energy to the spinal cord associated with regions of the body afflicted with chronic pain can induce "paresthesia" (a subjective sensation of numbness or tingling) in the afflicted bodily regions.

SCS therapy, delivered via epidurally implanted electrodes, is a widely used treatment for chronic intractable neuropathic pain of different origins. Traditional tonic therapy evokes paresthesia covering painful areas of a patient. During SCS therapy calibration, the paresthesia is identified and localized to the painful areas by the patient in connection with determining correct electrode placement.

Recently, new stimulation configurations such as burst stimulation and high frequency stimulation, have been developed, in which closely spaced high frequency pulses are delivered to the spinal cord in a manner that does not generate paresthesias for the majority of patients, but still affords a therapeutic result. Neuropathic pain may result from lesions or diseases affecting the peripheral or central regions of the somatosensory system, and is difficult to treat. The first spinal cord stimulator as a treatment for neuropathic pain was implanted by Shealy in 1967, which was based on the gate-control theory proposed by Melzack and Wall (1965). The gate-control theory proposed that the activation of large diameter A-beta (Aβ) fibers inhibits the transmission of noxious stimuli to the brain via an inhibitory interneuron. It has been shown that electrical stimulation also may activate these large A-beta fibers with the same result. The A-beta fibers transmit information from the periphery through the dorsal root ganglion (DRG) before projecting through the dorsal column.

Other types of sensory neurons (nerve cells) transmit information from the periphery through the DRG and terminate directly into the dorsal horn of the spinal cord. A-delta (A-delta) fibers are small lightly myelinated fibers that transmit mechanical or painful information, and may be perceived as the sharp pain felt after injury. C-fibers are the smallest and unmyelinated sensory neurons that transmit painful information to spinothalamic tract neurons (major pain pathway) in the dorsal horn and may be perceived as the dull ache after injury.

Currently, there has been no way to determine values for the therapy parameters that define burst and other high frequency waveform stimulation without first inducing paresthesias through delivery of tonic waveform stimulation.

SUMMARY

In accordance with one embodiment, a method is provided for controlling non-paresthesia stimulation of nervous tissue of a patient. The method comprises delivering a non-paresthesia stimulation waveform to at least one electrode located proximate to nervous tissue of interest, the non-paresthesia stimulation waveform including a series of pulses configured to excite at least one of A-delta fibers or C-fibers of the nerve tissue of interest. The non-paresthesia stimulation waveform is defined by therapy parameters. The method comprises sensing sensory action potential (SAP) signals from the nervous tissue of interest and analyzing the SAP signals to obtain activity data for at least one of an SAP C-fiber component or an SAP A-delta fiber component. The method also comprises determining whether the activity data satisfies the criteria of interest, and adjusting at least one of the therapy parameters to change the non-paresthesia stimulation waveform when the activity data does not satisfy the criteria of interest.

Optionally, the therapy parameters may define at least one of a burst stimulation waveform or a high frequency stimulation waveform. Optionally, a determining operation may include determining whether a high frequency content of the SAP signal falls below a threshold or within an acceptable range, thereby indicating that no pain or an acceptable low level of pain is experienced by the patient. Optionally, the method may comprise a determining operation which includes analyzing a pain-activity data relation to identify a pain score, the pain-activity data relation corresponding to a relation between high frequency content of the SAP signals and pain scores indicative of a level of pain experienced by the patient.

Optionally, the method may further comprise iteratively repeating the delivering, sensing and adjusting operations to optimize the non-paresthesia stimulation waveform. Optionally, the method may comprise an analyzing operation which includes analyzing a feature of interest from a morphology of the SAP signal over time, counting a number of occurrences of the feature of interest that occur within the SAP signal over a predetermined duration, and generating the activity data based on the number of occurrences of the feature of interest.

In accordance with an embodiment, a method is provided for controlling non-paresthesia stimulation of nervous tissue of a patient. The method comprises providing a lead having at least one electrode on the lead configured to be implanted at a target position proximate to nervous tissue of interest. The method also comprises delivering a non-paresthesia stimulation waveform to the at least one electrode based on a therapy parameter set (TPS), the stimulation waveform including a series of pulses configured to excite at least one of A-delta fibers or C-fibers of the nervous tissue of interest. The method comprises sensing sensory action potential (SAP) signals, iteratively repeating the delivering and sensing operations while changing at least one parameter from the TPS, and analyzing the SAP signals to obtain activity data associated with the TPS for at least one of an SAP C-fiber component or an SAP A-delta fiber component. The analyzing operations obtain a collection of activity data associated with multiple therapy parameter set.

Optionally, the method further comprises selecting a candidate TPS from the multiple therapy parameter set, wherein the candidate TPS selected has corresponding activity data that meets a criteria of interest. Optionally, the method may include a selecting operation which includes optimizing the candidate TPS to a stimulation configuration that affords a result of interest without inducing paresthesia. Optionally, the method may include an analyzing operation which identifies a high frequency content of at least one of the SAP C-fiber component or the A-delta fiber component within the SAP signals sensed.

Optionally, the method may further comprise applying a reference noxious input during an interval between successive burst waveforms, the reference noxious input creating the SAP signals sensed. Optionally, the method may further comprise changing at least one of the parameters for the TPS during each iteration through the delivering, sensing and analyzing operation. Optionally, the method may include the criteria of interest representing a number of peaks that occur in the SAP signal and the candidate TPS selected has the fewest number of peaks with respect to the multiple therapy parameter sets analyzed. Optionally, the method may include the therapy parameters defining at least one of a burst stimulation waveform or a high frequency stimulation waveform.

In accordance with another embodiment, a system is provided for controlling non-paresthesia stimulation of nervous tissue of a patient. The system comprises a lead having at least one stimulation electrode, the lead configured to be implanted at a target position proximate to nervous tissue of interest. The system also comprises an implantable pulse generator (IPG) coupled to the lead. The IPG is configured to deliver a stimulation waveform to at least one electrode based on a therapy parameter set (TPS), the stimulation waveform including a series of pulses configured to excite at least one of A-delta fibers or C-fibers of the nervous tissue. The IPG is coupled to a lead that senses sensory action potential (SAP) signals, and iteratively repeats the delivering and sensing operations while changing at least one parameter from the TPS. The IPG analyzes the SAP signals to obtain activity data associated with the TPS for at least one of an SAP C-fiber component or an SAP A-delta fiber component, the analyzing operations obtaining a collection of activity data associated with multiple therapy parameter sets (TPSs).

Optionally, the processor may be configured to select a candidate TPS from the multiple therapy parameter sets based on a criteria of interest related to the activity data, and utilize the candidate TPS in connection with delivering non-paresthesia therapy. Optionally, the system may further comprise memory configured to store a pain-activity data relation defining a relation between high frequency content of the SAP signals and pain scores indicative of pain experienced by a patient. Optionally, the system may include at least one electrode including a microelectrode configured to be located immediately adjacent C-fibers and configured to sense a C-fiber sensory action potential (SAP) directly at the microelectrode.

Optionally, the processor may be configured to receive a pain score indicative of a level of pain experienced by the patient in connection with each of the therapy parameter sets, the processor configured to define a relation between the activity data and the pain scores and save the relation in memory. Optionally, the therapy parameters may define at least one of a burst stimulation waveform or a high frequency stimulation waveform.

DETAILED DESCRIPTION

Figure 1:
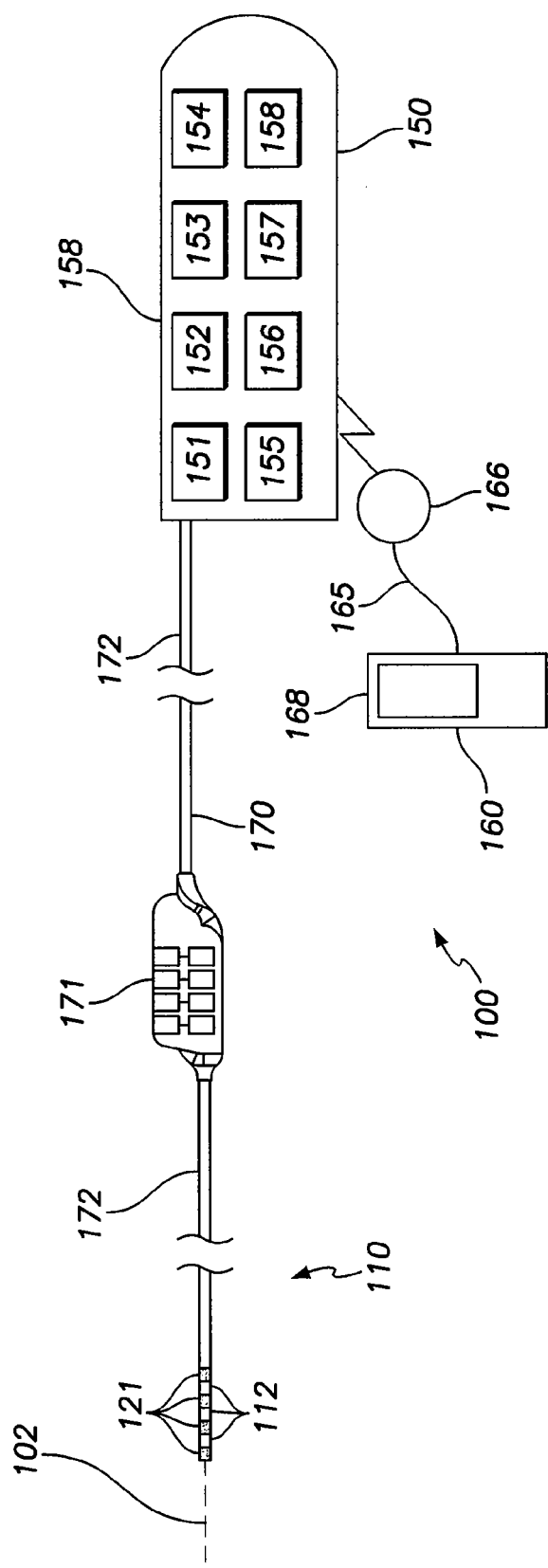
FIG. 1 illustrates a neurostimulation system, according to an embodiment of the present disclosure.

While multiple embodiments are described, still other embodiments of the described subject matter will become apparent to those skilled in the art from the following detailed description and drawings, which show and describe illustrative embodiments of disclosed inventive subject matter. As will be realized, the inventive subject matter is capable of modifications in various aspects, all without departing from the spirit and scope of the described subject matter. Accordingly, the drawings and detailed description are to be regarded as illustrative in nature and not restrictive.

In accordance with embodiments herein, methods and systems are provided that determine (e.g. optionally seek to optimize) alternative non-paresthesia stimulation therapies, such as burst and high frequency stimulation waveforms, for neurostimulation systems (SCS, PNS, PNfS and DRG stimulation) that do not invoke paresthesias, while still affording the ability to suppress the pain by stimulation leads placed epidurally or in other areas. The methods and systems determine non-paresthesia therapies based on A-delta and C-fiber sensory action potentials (SAP) sensed from the DRG or dorsal roots (DR). In accordance with embodiments herein, closed loop neurostimulation systems and methods are provided that sense the A-delta and C-fiber SAPs component from the DRG (or DR). One or more features of interest (e.g. frequency of SAP) from the A-delta and C-fiber SAP component are used as feedback to select settings for therapy parameters that define stimulation waveforms, such as burst and high frequency stimulation waveforms, frequencies as well as lead implant locations, thereby enabling both energy conservation and stimulation efficacy. The pain signals transmitted within A-delta and C fibers are spontaneously generated action potentials that appear as "spikes" in the electrical signal measured at the electrodes. The more pain felt, the higher the SAP frequency or spike frequency of the A-delta and C-fibers. The methods and systems herein, seek to suppress or ameliorate pain related SAPs conveyed by the A-delta fibers and/or C-fibers.

Nervous System Overview

The nervous system is comprised of the central nervous system (CNS) and the peripheral nervous system (PNS). The CNS contains the brain and spinal cord. The PNS is comprised mainly of mixed nerves, which are enclosed bundles of the long fibers or axons (endings of nerve cells or neurons) that connect the CNS to every other part of the body. There are two types of nerve fibers in a mixed nerve that include: sensory nerve fibers (afferent fibers sending information towards the brain) and motor nerve fibers (efferent fibers sending information from the brain). Sensory neurons transmit information from the environment, such as pain and motor neurons that mediate voluntary and involuntary movement.

In general, the peripheral nerve fibers may be classified into three types of nerve fibers based on the nerve fiber diameter and conduction velocity, namely A-, B- and C-fibers. A-fibers have large diameters, high conduction velocities, are highly myelinated, and are further subdivided by size and conduction velocity as A-alpha, A-beta, A-gamma and A-delta fibers. By way of example, the fast conduction velocity of the A-alpha fibers may be on the order of 80-120 m/s, and the A-alpha fibers may be on average 13-20 µm in diameter. B-fibers have diameters of about 3 um and conduction velocities of 3-15 m/s. C-fibers are small neurons with slow conduction velocities and are not myelinated.

A-delta fibers have conduction velocities on the order of 5-35 m/s, and the A-delta fibers may be on average 1.0-5.0 µm in diameter. A-delta fibers carry information mainly from the nociceptive-mechanical or mechanothermal-specific stimuli and are considered nociceptors. Their receptive fields (area of innervation) are small, and therefore, provide precise localization of pain.

C-fibers are unmyelinated, have a small diameter and low conduction velocity. By way of example, the slow conduction velocity of the C-fibers may be on the order of 0.5-2.0 m/s, and the C-fibers may be on average 0.2-1.5 µm in diameter. C-fibers carry sensory information, such as nociception (pain), temperature, and itch. C-fibers are unmyelinated unlike most other fibers in the nervous system. The lack of myelination is, at least in part, a cause of the slow conduction velocity attributed to C-fibers.

C-fibers are activated by and carry information from a variety of high-intensity mechanical, chemical and thermal stimulation and thus are considered as polymodal nociceptors. C-fibers comprise about 70% of all the fibers carrying noxious input. The receptive field of these neurons is large and, therefore, less precise for pain localization.

The cell bodies of all primary afferent pain neurons from the body, face, and head are located in the dorsal root ganglia (DRG) and in the trigeminal ganglia respectively. Some of these cell bodies have myelinated axons (A-delta fibers), and others have unmyelinated axons (C-fibers). Both A-delta fiber's and the unmyelinated C-fiber's axons have free nerve endings, which innervate the same areas in the periphery.

A-delta fibers are responsible for the sensation of a quick shallow pain that is specific on one area, termed as first pain. The A-delta fibers respond to a weaker intensity of noxious stimulus. C-fibers respond to noxious stimuli which have stronger intensities and account for the slow, but deeper second pain that spreads out over an unspecific area.

Nociception is the response to painful stimuli transmitted via sensory action potentials of A-delta and C-fibers. SCS therapy may decrease the frequency of the nociceptive action potentials with varying efficacy as the therapy parameters change. Burst and high frequency type SCS therapies can be controlled by adjusting relevant parameters to modulate the charge delivered to the spinal cord during stimulation. As explained herein, the efficacy of burst and high frequency waveform stimulations may be dependent on certain therapy parameters, more so than other therapy parameters (e.g. dependent on the charge per burst).

Figure 4A:
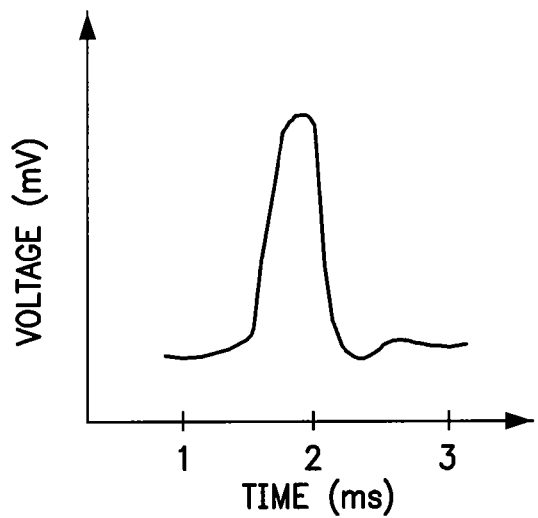
FIG. 4A illustrates an action potential measured from a C-fiber, without prior delivery of a non-paresthesia therapy in accordance with embodiments herein.

FIG. 4A illustrates an action potential measured from a C-fiber, without prior delivery of a non-paresthesia therapy. The vertical axis represents the voltage potential measured by the electrodes, and the horizontal axis represents time. When an external input (e.g. pain) occurs at an area of interest on a patient, action potentials are conveyed along the C-fibers and A-delta fibers. Action potentials include numerous peaks and valleys, generally referred to as spikes or direction changes. The magnitude of the spikes/direction changes, as well as the rate of occurrence (frequency) for the spikes/direction changes, correlate with a severity of the external input (e.g. pain or pain scores that measured at clinics). In accordance with embodiments herein, the magnitude and rate of occurrence of the spikes/direction changes are suppressed when an appropriate non-paresthesia therapy is delivered.

Figure 4B:
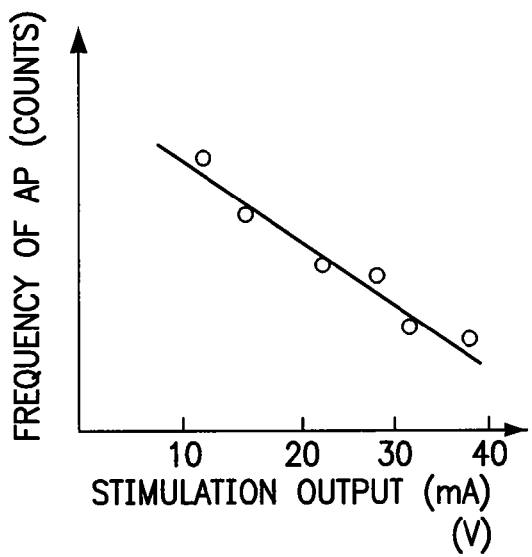
FIG. 4B illustrates an example plotting a relation between the non-paresthesia therapy and the frequency of action potentials conveyed along the C-fibers and/or A-delta fibers.

FIG. 4B illustrates an example plotting a relation between the non-paresthesia therapy and the frequency of action potentials conveyed along the C-fibers and/or A-delta fibers. The horizontal axis corresponds to the energy (in milliamps) delivered from the lead electrode by the non-paresthesia therapy. The vertical axis corresponds to a count of the number of spikes/direction changes (frequency) in the action potential. As shown in FIG. 4B, as the energy level is increased from 10 to 40 mA, the number of spikes in the action potential decreases.

Figure 3A:
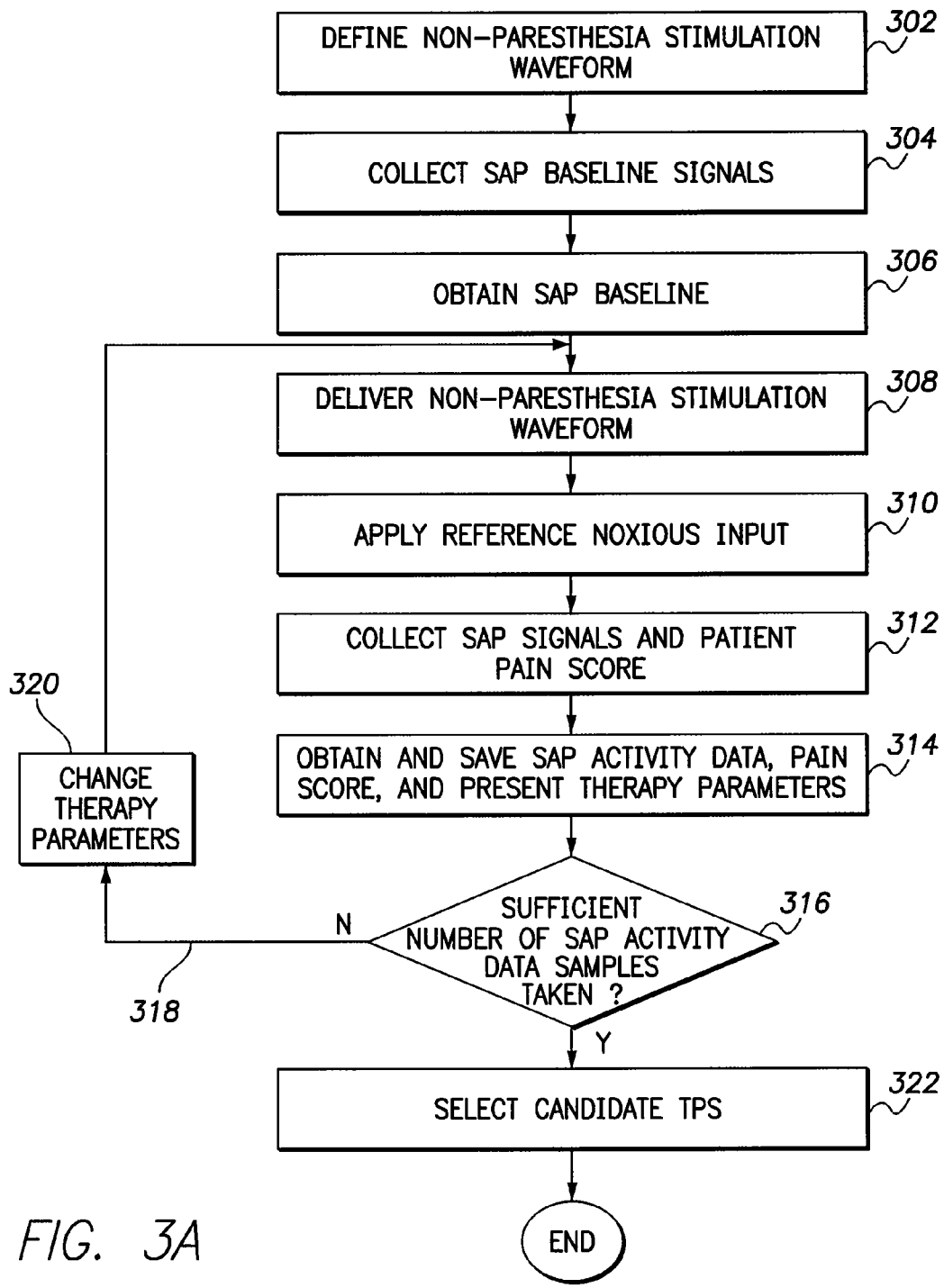
FIG. 3A illustrates a process for collecting and analyzing activity data in connection with multiple therapy parameter sets in accordance with embodiments herein.
Figure 3B:
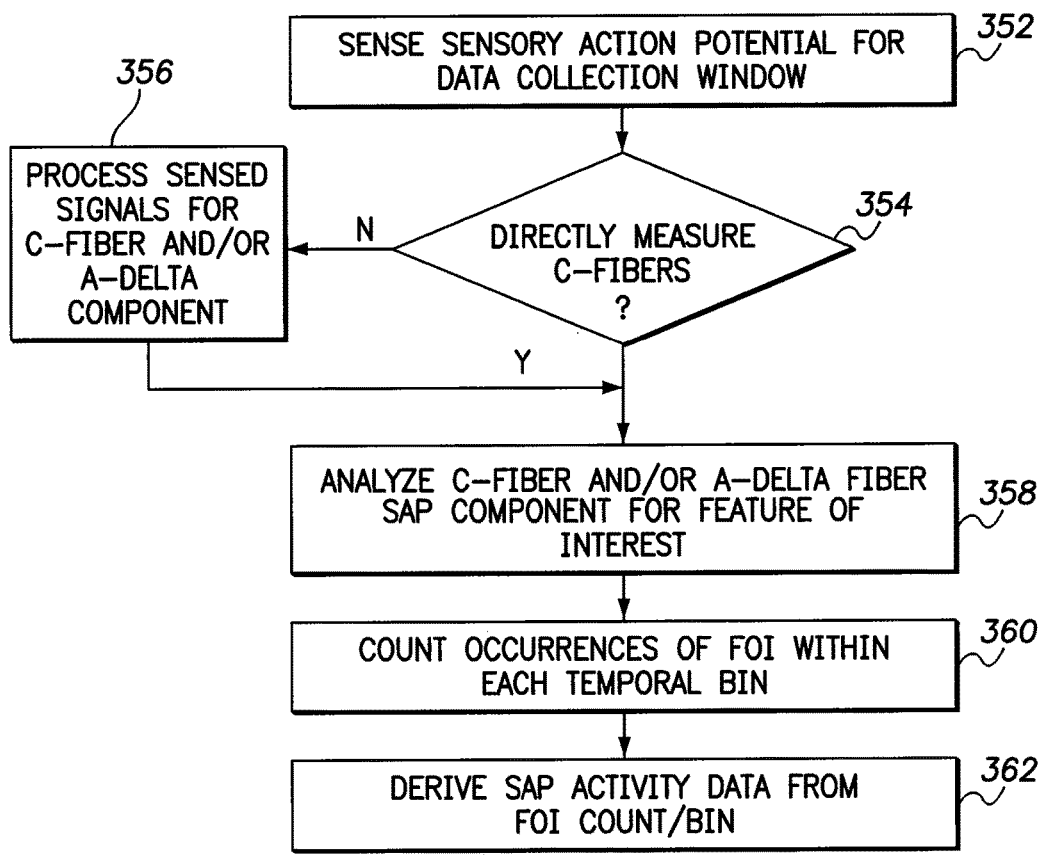
FIG. 3B illustrates a process for collecting and analyzing SAP signals to obtain SAP activity level data in connection with the operations of FIG. 3A in accordance with embodiments herein.
Figure 3C:
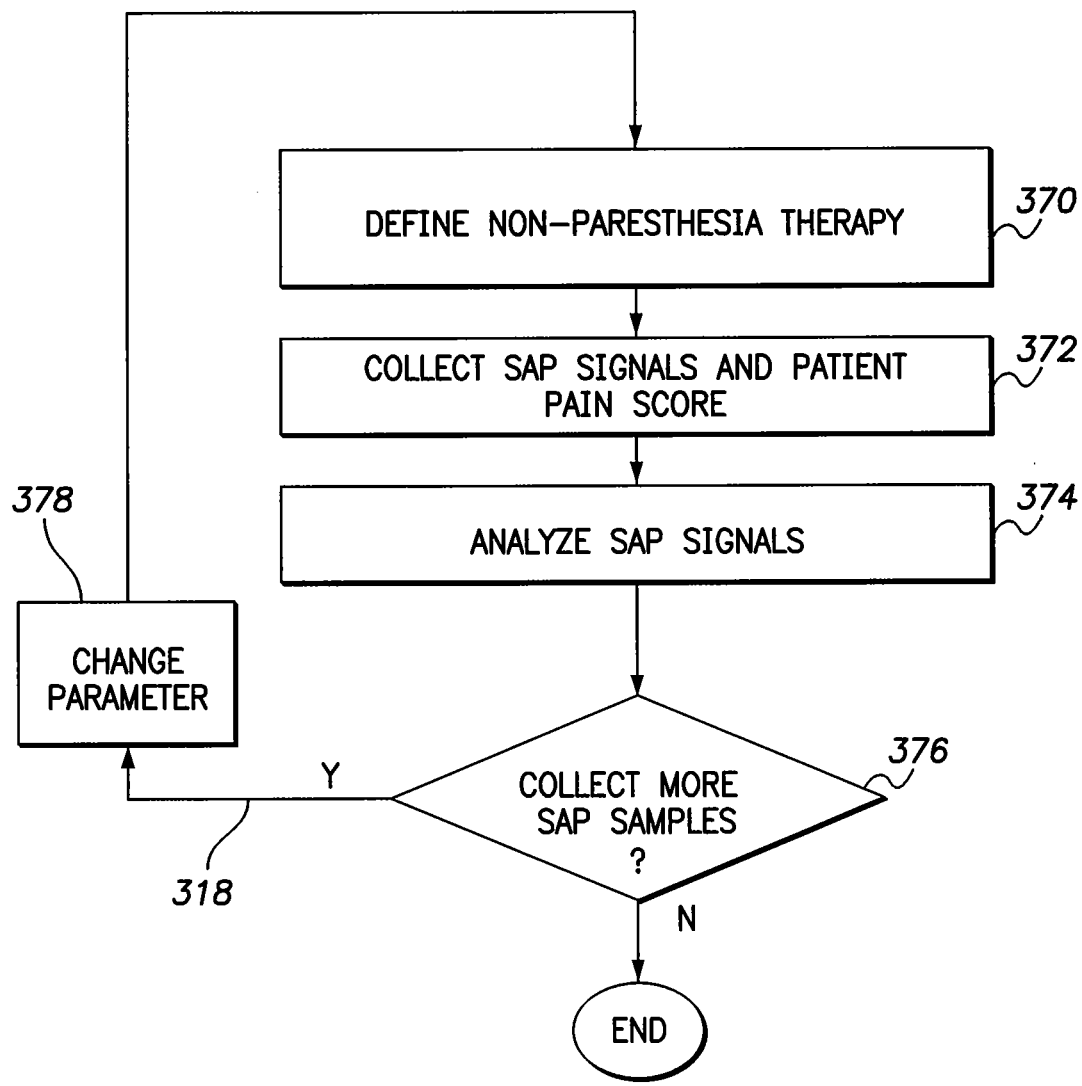
FIG. 3C illustrates a process for generating a correlation between pain scores and activity data (e.g. high frequency content) in connection with multiple non-paresthesia therapies in accordance with embodiments herein.
Figure 3D:
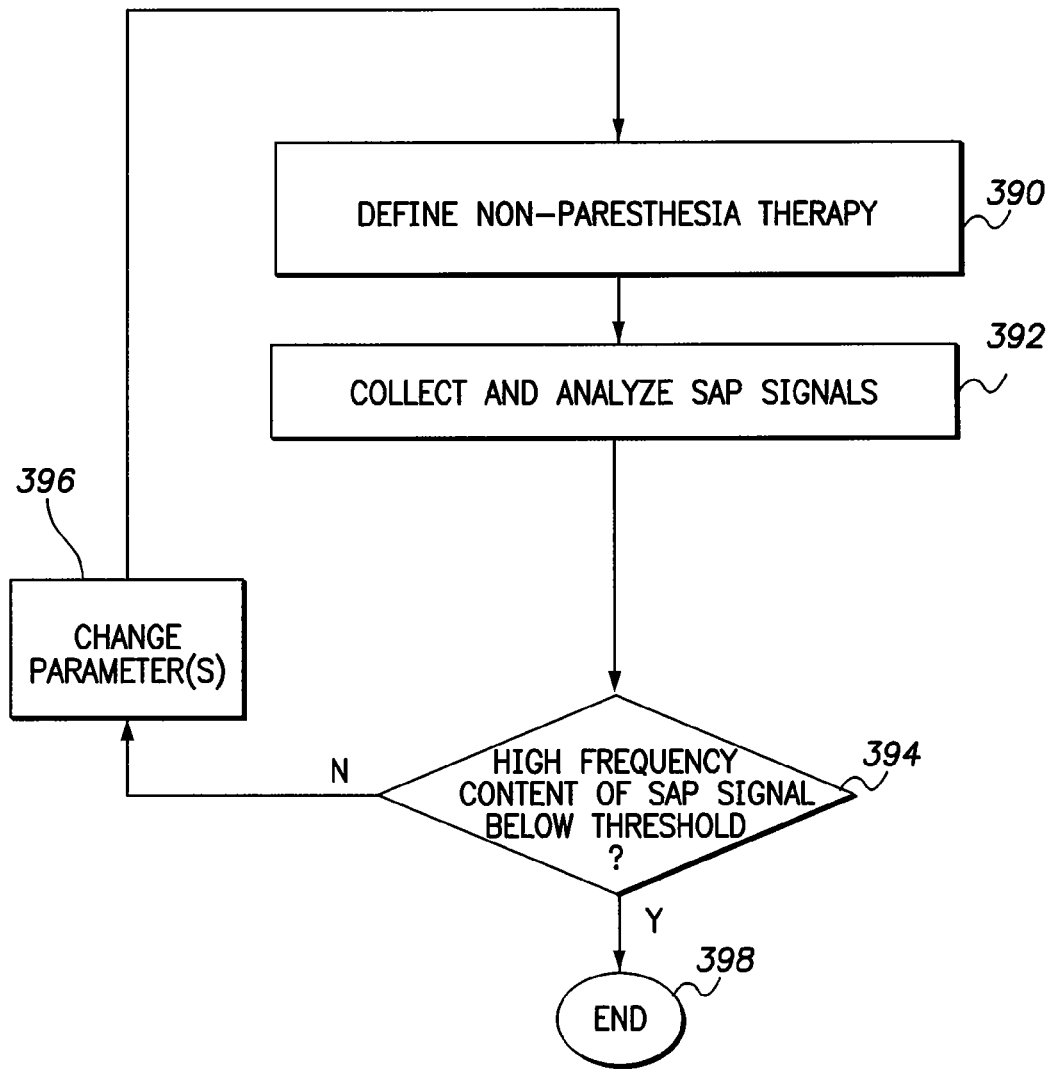
FIG. 3D illustrates a process for selecting a non-paresthesia therapy in accordance with embodiments herein.
Figure 4C:
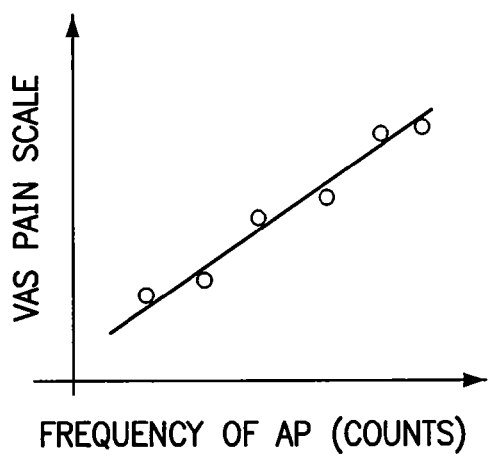
FIG. 4C illustrates an example plotting a relation between the frequency of the action potential relative to a pain scale.
Figure 5A:
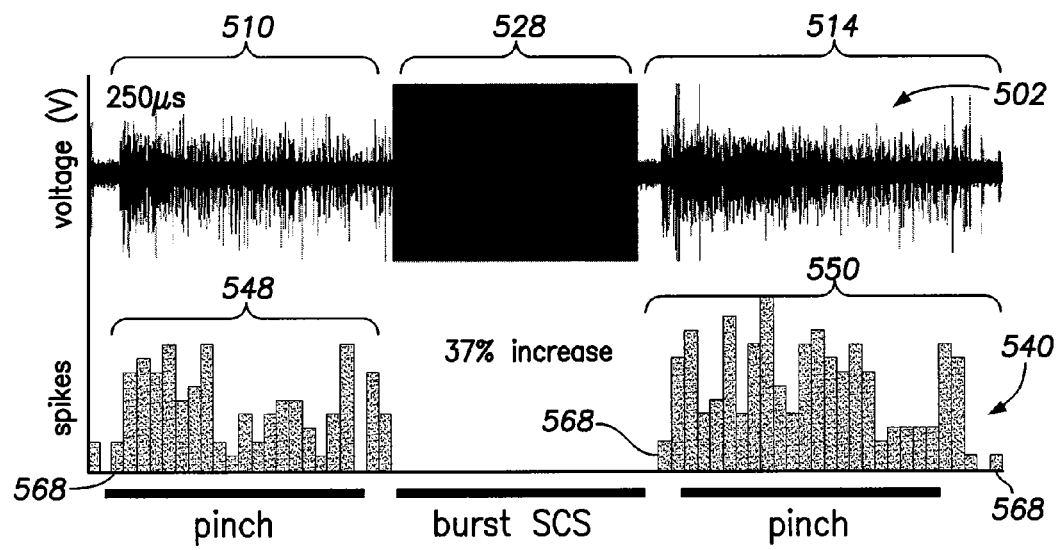
FIGS. 5A-5D illustrate examples of sensory action potential signals collected in accordance with embodiments herein.
Figure 5B:
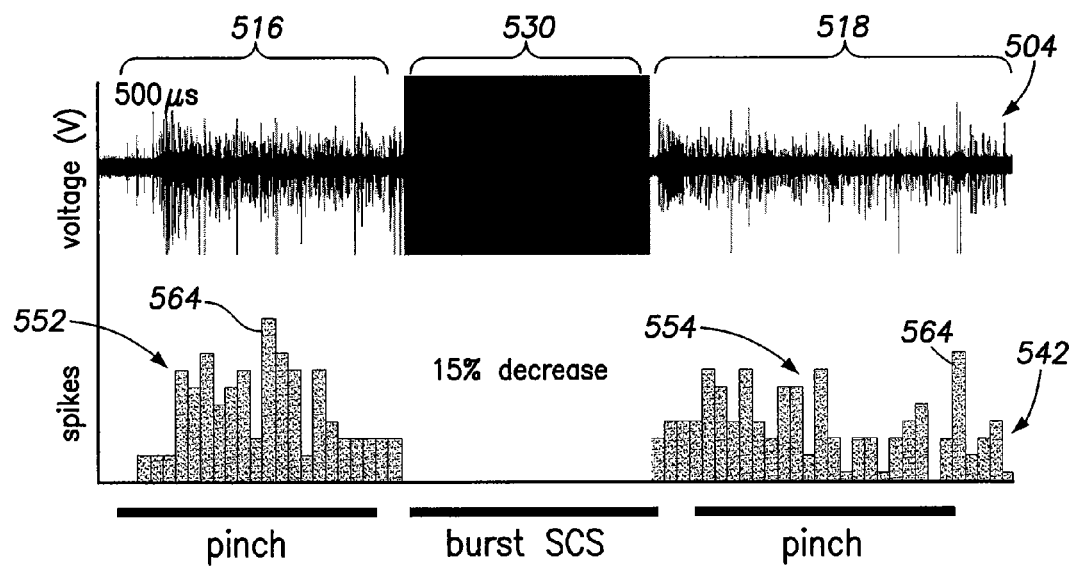
Figure 5C:
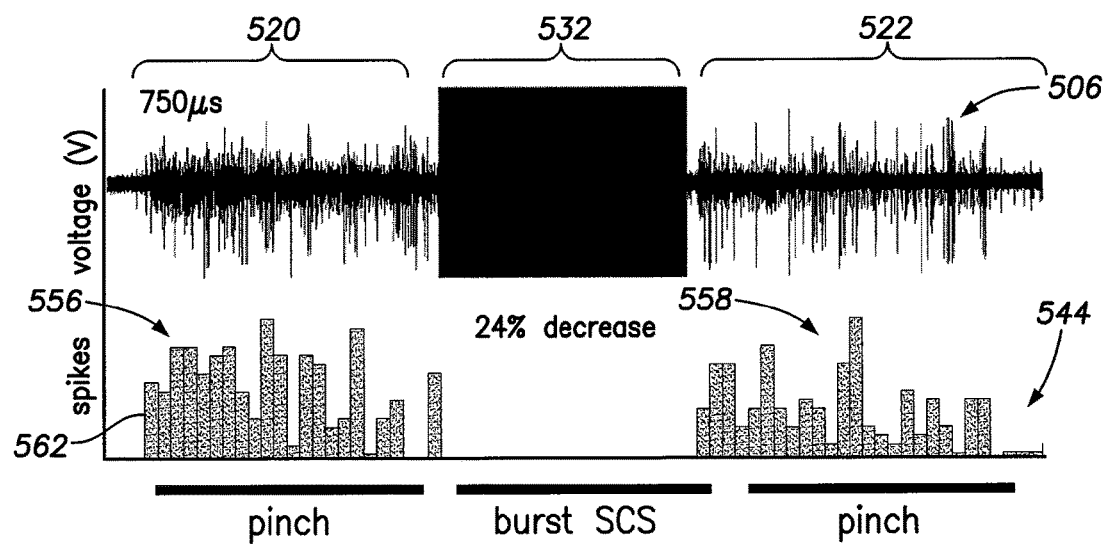
Figure 5D:
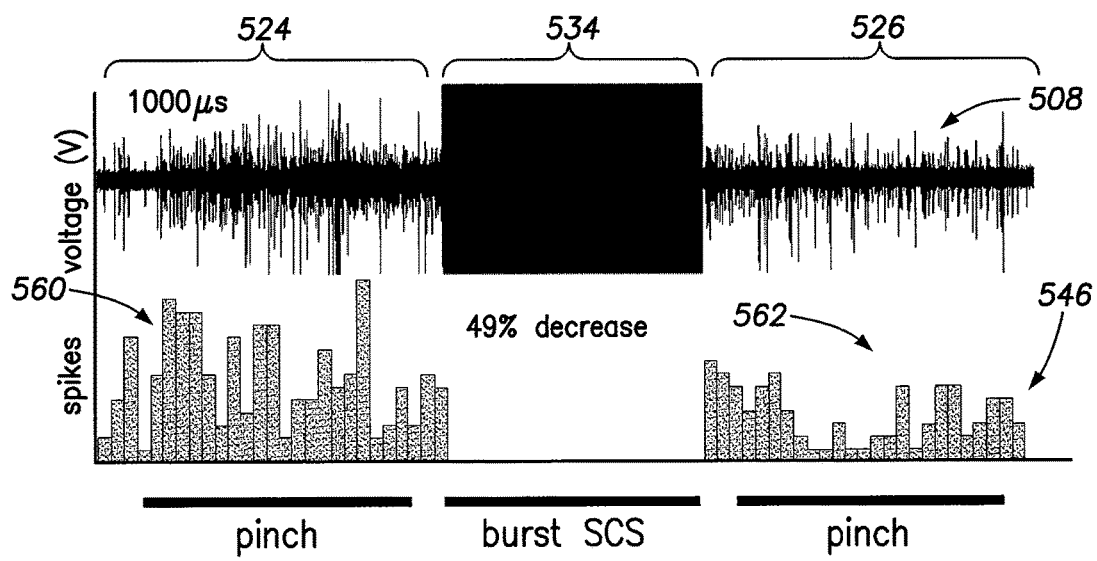

FIG. 4C illustrates an example plotting a relation between the frequency of the action potential relative to a pain scale measured. The horizontal axis corresponds to the frequency of the action potentials conveyed along the C-fibers and/or A-delta fibers. The vertical axis corresponds to the pain scale, which represents a visual analog scale, for which values are provided by a patient during testing. As explained below in connection with FIGS. 3A-3D, after implant of an NS system 100, non-paresthesia therapy is delivered. The therapy parameters, defining burst or high frequency stimulation waveforms, may be varied (e.g., number of burst, intervals, pulse duration, pulse amplitude etc., and lead implant locations) between each VAS or NRS rating. The high frequency content of action potentials is identified from the SAP signals in connection with each non-paresthesia therapy. In addition, the patient is asked to provide a pain score and the measured frequency of the action potentials (AP) is correlated to the pain scores. The patient is requested to note his/her pain intensity score, e.g. visual analog scale (VAS) or numeric rating scale (NRS) or based on another pain scale, in connection with each non-paresthesia therapy. FIG. 4C represents an example of how a patient's VAS may vary as a function of the frequency of AP. In the example of FIG. 4C, the function represents a linear relationship, such that the correlation coefficient is the slope of the curve and the unit is "pain score per ρV". Optionally, a non-linear relationship may be determined as the pain per unit measure.

In accordance with embodiments herein, a programmer is provided that is configured to select therapy parameters that define a non-paresthesia therapy that achieves a desired result. After implantation of the NS system 100, an intra-operative programming session may be conducted while the patient remains under general or local anesthetic. The SAP signals are recorded and visualized, such as on the clinician's programmer, patient programmer or an external device. The high frequency content of APs is then extracted from the SAP signals, converted to the VAS according to the calibration test (e.g., of FIG. 3C), and is shown on the programmer. Then the parameters of the alternative stimulation (such as number of bursts, intervals, pulse duration, pulse amplitude, etc.) may be changed until the frequency of action potentials from A-delta and C fibers are reduced to a desired level, such as minimized or completely disappear. During subsequent programming sessions, the frequency of APs from A-delta and C fibers may be monitored from the same recording electrode and compared to the "AP frequency" generated from "the maximal tolerant pain", and thus, provide feedback to the NS system 100 to further change/optimize/control the stimulation parameters.

To determine a select placement of the SCS leads, the DRG and SCS leads may be placed into respective implant locations. The frequency of APs may be measured from the A-delta and C fibers. The SCS stimulation lead may be moved until a select placement is determined based on reduction of A-delta and C fiber APs (e.g., optional placement may correspond to a maximum reduction of APs).

In accordance with embodiments, for ambulatory monitoring, after implant, the NS system 100 stimulates the spinal cord or DRG for pain relief, while sampling measures of APs. The NS system 100 converts the AP measures to a pain score using a correlation coefficient (e.g. as predefined in FIG. 4C) and saves the pain score to the memory of the NS system 100 for downloading later or sends to the network database for diagnostic purpose by a pain physician. In an ambulatory state, the NS system 100 will record the AP from the leads after stimulation, compare the frequency of APs associated with each pain scale, and change the stimulation levels until the frequency of APs detected are reduced by a select amount (e.g., optimizing the stimulation output).

System Overview

FIG. 1 depicts an NS system 100 that generates electrical pulses for application to tissue of a patient according to one embodiment. For example, the NS system 100 may be adapted to stimulate spinal cord tissue, peripheral nervous tissue, deep brain tissue, cortical tissue, cardiac tissue, digestive tissue, pelvic floor tissue, or any other suitable nervous tissue of interest within a patient's body.

The NS system 100 may be controlled to deliver various types of non-paresthesia therapy, such as high frequency neurostimulation therapies, burst neurostimulation therapies and the like. High frequency neurostimulation includes a continuous series of monophasic or biphasic pulses that are delivered at a predetermined frequency (such as 2-10K). Burst neurostimulation includes short sequences of monophasic or biphasic pulses, where each sequence is separated by a quiescent period. By way of example, the pulses within each burst sequence may be delivered with an intraburst frequency of about 500 Hz. In general, non-paresthesia therapies include a continuous, repeating or intermittent pulse sequence delivered at a frequency and amplitude configured to avoid inducing (or introduce a very limited) paresthesia.

The NS system 100 may represent a closed loop neurostimulation device, where the new device is configured to provide real-time sensing functions for A-delta and C-fiber action potential (APs) from a dorsal root ganglion (DRG) lead. The configuration of the lead sensing electrodes that sense action potentials from the A-delta and C fibers may be varied depending on the neuronal anatomy of the sensing site(s) of interest. The size and shape of electrodes is varied based on the implant location, such as the dorsal root (DR) or DRG. By way of example only, a laminectomy procedure may be used, in order to obtain accurate action potential signals indicative of pain from the C fiber and/or the A-delta fiber. The electronic components within the NS system 100 are designed with both stimulation and sensing capabilities, including alternative non-paresthesia stimulation therapy, such as burst mode, high frequency mode and the like. The NS system 100 detects A-delta and C-fiber action potentials from a patient's painful area and qualify A-delta and C-fiber action potential signals based on a predetermined pain scale. Changes to the frequency of the A-delta and C-fiber action potential signals is used to guide parameter settings for the non-paresthesia stimulation therapy, such as to define burst or high frequency parameters. In one embodiment, one lead stimulates the dorsal column, the second lead senses from DRG or DR. In another embodiment, the lead can stimulate DRG or DR and sense from the same stimulation location.

The NS system 100 includes an implantable pulse generator (IPG) 150 that is adapted to generate electrical pulses for application to tissue of a patient. The IPG 150 typically comprises a metallic housing or can 158 that encloses a controller 151, pulse generating circuitry 152, a charging coil 153, a battery 154, a far-field and/or near field communication circuitry 155, battery charging circuitry 156, switching circuitry 157, memory 158 and the like. The controller 151 typically includes a microcontroller or other suitable processor for controlling the various other components of the device. Software code is typically stored in memory of the IPG 150 for execution by the microcontroller or processor to control the various components of the device.

The IPG 150 may comprise a separate or an attached extension component 170. If the extension component 170 is a separate component, the extension component 170 may connect with the "header" portion of the IPG 150 as is known in the art. If the extension component 170 is integrated with the IPG 150, internal electrical connections may be made through respective conductive components. Within the IPG 150, electrical pulses are generated by the pulse generating circuitry 152 and are provided to the switching circuitry 157. The switching circuitry 157 connects to outputs of the IPG 150. Electrical connectors (e.g., "Bal-Seal" connectors) within the connector portion 171 of the extension component 170 or within the IPG header may be employed to conduct various stimulation pulses. The terminals of one or more leads 110 are inserted within connector portion 171 or within the IPG header for electrical connection with respective connectors. Thereby, the pulses originating from the IPG 150 are provided to the leads 110. The pulses are then conducted through the conductors of the lead 110 and applied to tissue of a patient via stimulation electrodes 121 that are coupled to blocking capacitors. Any suitable known or later developed design may be employed for connector portion 171.

The stimulation electrodes 121 may be positioned along a horizontal axis 102 of the lead 110, and are angularly positioned about the horizontal axis 102 so the stimulation electrodes 121 do not overlap. The stimulation electrodes 121 may be in the shape of a ring such that each stimulation electrode 121 continuously covers the circumference of the exterior surface of the lead 110. Each of the stimulation electrodes 121 are separated by non-conducting rings 112, which electrically isolate each stimulation electrode 121 from an adjacent stimulation electrode 121. The non-conducting rings 112 may include one or more insulative materials and/or biocompatible materials to allow the lead 110 to be implantable within the patient. Non-limiting examples of such materials include polyimide, polyetheretherketone (PEEK), polyethylene terephthalate (PET) film (also known as polyester or Mylar), polytetrafluoroethylene (PTFE) (e.g., Teflon), or parylene coating, polyether bloc amides, polyurethane. The stimulation electrodes 121 may be configured to emit the pulses in an outward radial direction proximate to or within a stimulation target. Additionally or alternatively, the stimulation electrodes 121 may be in the shape of a split or non-continuous ring such that the pulse may be directed in an outward radial direction adjacent to the stimulation electrodes 121. The stimulation electrodes 121 deliver high frequency and/or burst stimulation waveforms as described herein. The electrodes 121 may also sense sensory action potential (SAP signals) for a data collection window. Optionally, the delivering operation may deliver the one stimulation waveform to a first sub-set of the electrodes and another stimulation waveform to a second sub-set of the electrodes, where the first and second sub-sets have at least one unique electrode relative to each other.

Optionally, the electrodes may include a microelectrode located immediately adjacent C-fibers. The method may sense a C-fiber sensory action potential (SAP) directly at the microelectrode and perform an iterative feedback loop to adjust at least one therapy parameter based on the A-delta or C-fiber SAP.

The lead 110 may comprise a lead body 172 of insulative material about a plurality of conductors within the material that extend from a proximal end of lead 110, proximate to the IPG 150, to its distal end. The conductors electrically couple a plurality of the stimulation electrodes 121 to a plurality of terminals (not shown) of the lead 110. The terminals are adapted to receive electrical pulses and the stimulation electrodes 121 are adapted to apply the pulses to the stimulation target of the patient. Also, sensing of physiological signals may occur through the stimulation electrodes 121, the conductors, and the terminals. It should be noted that although the lead 110 is depicted with four stimulation electrodes 121, the lead 110 may include any suitable number of stimulation electrodes 121 (e.g., less than four, more than four) as well as terminals, and internal conductors. Additionally or alternatively, various sensors (e.g., a position detector, a radiopaque fiducial) may be located near the distal end of the lead 110 and electrically coupled to terminals through conductors within the lead body 172.

Although not required for any embodiments, the lead body 172 of the lead 110 may be fabricated to flex and elongate upon implantation or advancing within the tissue (e.g., nervous tissue) of the patient towards the stimulation target and movements of the patient during or after implantation. By fabricating the lead body 172, according to some embodiments, the lead body 172 or a portion thereof is capable of elastic elongation under relatively low stretching forces. Also, after removal of the stretching force, the lead body 172 may be capable of resuming its original length and profile. For example, the lead body may stretch 10%, 20%, 25%, 35%, or even up or above to 50% at forces of about 0.5, 1.0, and/or 2.0 pounds of stretching force. Fabrication techniques and material characteristics for "body compliant" leads are disclosed in greater detail in U.S. Provisional Patent Application No. 60/788,518, entitled "Lead Body Manufacturing," which is expressly incorporated herein by reference.

Figure 2C:
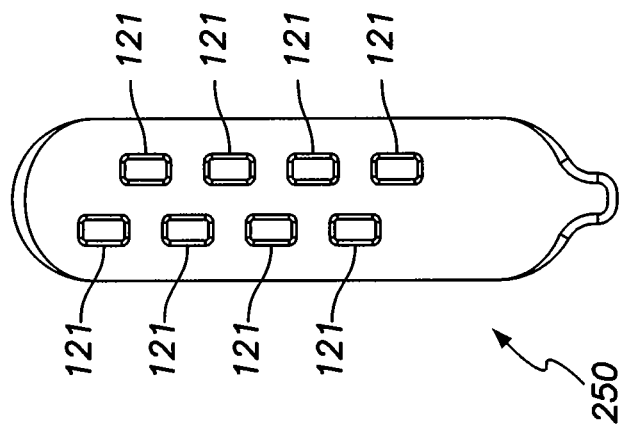
FIGS. 2A-2C depict stimulation portions for inclusion at the distal end of lead.
Figure 2B:
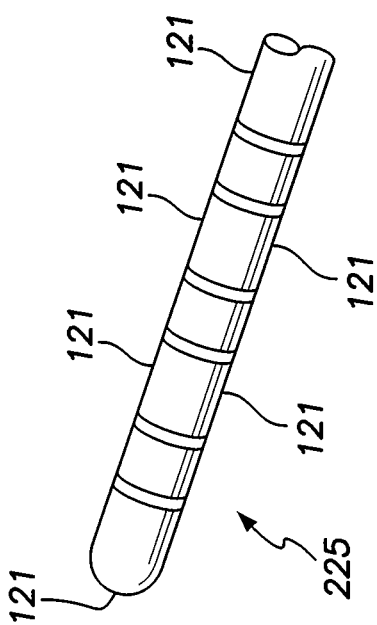
Figure 2A:
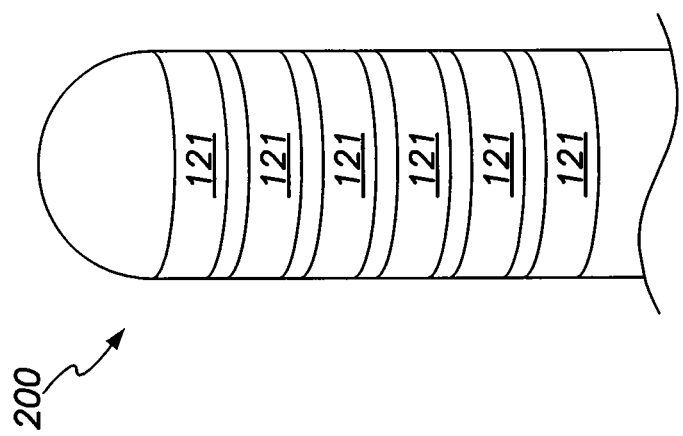

FIGS. 2A-2C respectively depict stimulation portions 200, 225, and 250 for inclusion at the distal end of lead 110. Stimulation portion 200 depicts a conventional stimulation portion of a "percutaneous" lead with multiple ring electrodes. Stimulation portion 225 depicts a stimulation portion including several segmented electrodes. Example fabrication processes are disclosed in U.S. patent application Ser. No. 12/895,096, entitled, "METHOD OF FABRICATING STIMULATION LEAD FOR APPLYING ELECTRICAL STIMULATION TO TISSUE OF A PATIENT," which is incorporated herein by reference. Stimulation portion 250 includes multiple planar electrodes on a paddle structure. Returning to FIG. 1, for implementation of the components within the IPG 150, a processor and associated charge control circuitry for an IPG is described in U.S. Pat. No. 7,571,007, entitled "SYSTEMS AND METHODS FOR USE IN PULSE GENERATION," which is expressly incorporated herein by reference. Circuitry for recharging a rechargeable battery (e.g., battery charging circuitry 156) of an IPG using inductive coupling and external charging circuits are described in U.S. Pat. No. 7,212,110, entitled "IMPLANTABLE DEVICE AND SYSTEM FOR WIRELESS COMMUNICATION," which is expressly incorporated herein by reference.

An example and discussion of "constant current" pulse generating circuitry (e.g., pulse generating circuitry 152) is provided in U.S. Patent Publication No. 2006/0170486 entitled "PULSE GENERATOR HAVING AN EFFICIENT FRACTIONAL VOLTAGE CONVERTER AND METHOD OF USE," which is expressly incorporated herein by reference. One or multiple sets of such circuitry may be provided within the IPG 150. Different burst and/or high frequency pulses on different stimulation electrodes 121 may be generated using a single set of the pulse generating circuitry 152 using consecutively generated pulses according to a "multi-stimset program" as is known in the art. Complex pulse parameters may be employed such as those described in U.S. Pat. No. 7,228,179, entitled "Method and apparatus for providing complex tissue stimulation patterns," and International Patent Publication Number WO 2001/093953 A1, entitled "NEUROMODULATION THERAPY SYSTEM," which are expressly incorporated herein by reference. Alternatively, multiple sets of such circuitry may be employed to provide pulse patterns (e.g., tonic stimulation waveform, burst stimulation waveform) that include generated and delivered stimulation pulses through various stimulation electrodes of one or more leads 121 as is also known in the art. Various sets of parameters may define the pulse characteristics and pulse timing for the pulses applied to the various stimulation electrodes 121. Although constant current pulse generating circuitry is contemplated for some embodiments, any other suitable type of pulse generating circuitry may be employed such as constant voltage pulse generating circuitry.

The controller 151, among other things, comprises a lead having at least one stimulation electrode, the lead configured to be implanted at a target position proximate to nervous tissue of interest; and an implantable pulse generator (IPG)

coupled to the lead. The controller 151 delivers a non-paresthesia stimulation waveform to at least one electrode located proximate to nervous tissue of interest, the non-paresthesia stimulation waveform including a series of pulses configured to excite at least one of A-delta fibers or C-fibers of the nervous tissue of interest, the non-paresthesia stimulation waveform defined by therapy parameters. The controller 151 senses sensory action potential (SAP) signals from at least one electrode on the lead. The controller 151 analyzes the SAP signals to obtain activity data for at least one of an SAP C-fiber component or an SAP A-delta fiber component. The controller 151 determines whether the activity data satisfies a criteria of interest. The controller 151 adjusts at least one of the therapy parameters to change the non-paresthesia stimulation waveform when the activity data does not satisfy the criteria of interest.

The controller 151 iteratively repeats the delivering and sensing operations for a group of TPS. The IPG analyzes the SAP signals to obtain activity data associated with the TPS for at least one of SAP C-fiber components or SAP A-delta fiber components, the analyzing operations obtaining a collection of activity data associated with the group of TPS. The IPG selects a candidate TPS from the group of TPS based on a criteria of interest.

The therapy parameters define at least one of a burst stimulation waveform or a high frequency stimulation waveform. The controller 151 may determine whether a high frequency content of the SAP signal falls below a threshold or within an acceptable range, thereby indicating that no pain or an acceptable low level of pain is experienced by the patient. The controller 151 may analyze a pain-activity data relation to identify a pain score, the pain-activity data relation corresponding to a relation between high frequency content of the SAP signals and pain scores indicative of a level of pain experienced by the patient. The controller 151 repeats the delivering, sensing and adjusting operations to optimize the non-paresthesia stimulation waveform. The analyzing operation may include analyzing a feature of interest from a morphology of the SAP signal over time, counting a number of occurrences of the feature of interest that occur within the SAP signal over a predetermined duration, and generating the activity data based on the number of occurrences of the feature of interest.

The controller 151 is configured to select a candidate TPS from the multiple therapy parameter sets based on a criteria of interest related to the activity data, and utilize the candidate TPS in connection with delivering non-paresthesia therapy. The controller 151 is configured to receive a pain score indicative of a level of pain experienced by the patient in connection with each of the therapy parameter sets. The controller 151 is configured to define a relation between the activity data and the pain scores and save the relation in memory. The therapy parameters define at least one of a burst stimulation waveform or a high frequency stimulation waveform.

Optionally, the controller 151 may be configured wherein the lead includes a plurality of electrodes, and the IPG is configured to deliver wherein the at least one electrode includes a microelectrode configured to be located immediately adjacent C-fibers and configured to sense a C-fiber sensory action potential (SAP) directly at the microelectrode. Optionally, the controller 151 may be configured wherein the processor adjusts the TPS for the burst waveform based on the C-fiber SAP component of the signals.

The controller 151 identifies a C-fiber and/or A-delta SAP components of the signals. The controller 151 further comprises comprising adjusting the therapy parameters based on the C-fiber and/or A-delta SAP components of the signals. The controller 151 adjusting operation includes adjusting the burst frequency to reduce the C-fiber SAP component. The controller 151 further comprises analyzing a feature of interest from a morphology of the C-fiber and/or A-delta SAP components over time, counting a number of occurrences of the feature of interest that occur within the C-fiber and/or A-delta SAP components over a predetermined duration, comparing the number of occurrences to a prior number of occurrences, and adjusting the parameter settings based on the comparing operation.

Memory 158 stores software to control operation of the controller 151 for coupled tonic/burst therapy as explained herein. The memory 158 also stores SAP signals, therapy parameters, SAP activity level data, pain scales and the like. For example, the memory 158 may save SAP activity level data for various different therapies as applied over a short or extended period of time. A collection of SAP activity level data is accumulated for different therapies and may be compared to identify high, low and acceptable amounts of sensory activity for the A-delta and/or C-fibers that result from different therapies. The memory 158 stores a pain-activity data relation defining a relation between high frequency content of the SAP signals and pain scores indicative of pain experienced by a patient.

A controller device 160 may be implemented to charge/recharge the battery 154 of the IPG 150 (although a separate recharging device could alternatively be employed) and to program the IPG 150 on the pulse specifications while implanted within the patient. Although, in alternative embodiments separate programmer devices may be employed for charging and/or programming the NS system 100. The controller device 160 may be a processor-based system that possesses wireless communication capabilities. Software may be stored within a non-transitory memory of the controller device 160, which may be executed by the processor to control the various operations of the controller device 160. A "wand" 165 may be electrically connected to the controller device 160 through suitable electrical connectors (not shown). The electrical connectors may be electrically connected to a telemetry component 166 (e.g., inductor coil, RF transceiver) at the distal end of wand 165 through respective wires (not shown) allowing bi-directional communication with the IPG 150. Optionally, in some embodiments, the wand 165 may comprise one or more temperature sensors for use during charging operations.

The user may initiate communication with the IPG 150 by placing the wand 165 proximate to the NS system 100. Preferably, the placement of the wand 165 allows the telemetry system of the wand 165 to be aligned with the far-field and/or near field communication circuitry 155 of the IPG 150. The controller device 160 preferably provides one or more user interfaces 168 (e.g., touchscreen, keyboard, mouse, buttons, or the like) allowing the user to operate the IPG 150. The controller device 160 may be controlled by the user (e.g., doctor, clinician) through the user interface 168 allowing the user to interact with the IPG 150. The user interface 168 may permit the user to move electrical stimulation along and/or across one or more of the lead(s) 110 using different stimulation electrode 121 combinations, for example, as described in U.S. Patent Application Publication No. 2009/0326608, entitled "METHOD OF ELECTRICALLY STIMULATING TISSUE OF A PATIENT BY SHIFTING A LOCUS OF STIMULATION AND SYSTEM EMPLOYING THE SAME," which is expressly incorporated herein by reference.

Also, the controller device 160 may permit operation of the IPG 150 according to one or more therapies to treat the patient. Each therapy may include one or more sets of stimulation parameters of the pulse including pulse amplitude, pulse width, pulse frequency or inter-pulse period, pulse repetition parameter (e.g., number of times for a given pulse to be repeated for respective stimset during execution of program), biphasic pulses, monophasic pulses, etc. The IPG 150 modifies its internal parameters in response to the control signals from the controller device 160 to vary the stimulation characteristics of the stimulation pulses transmitted through the lead 110 to the tissue of the patient. NS systems, stimsets, and multi-stimset programs are discussed in PCT Publication No. WO 2001/093953, entitled "NEUROMODULATION THERAPY SYSTEM," and U.S. Pat. No. 7,228,179, entitled "METHOD AND APPARATUS FOR PROVIDING COMPLEX TISSUE STIMULATION PATTERNS," which are expressly incorporated herein by reference.

FIGS. 3A-3D illustrate processes for controlling non-paresthesia (e.g. burst and/or high frequency) stimulation of nervous tissue of a patient in accordance with embodiments herein. The operations of FIGS. 3A-3D may be implemented by one or more processors, such as within an implantable pulse generator, external programmer, another external device and the like. The IPG, external programmer or other external device are coupled to a lead having at least one stimulation electrode that is implanted at a target position proximate to nervous tissue of interest.

FIG. 3A illustrates a process for collecting and analyzing activity data in connection with multiple therapy parameter sets in accordance with embodiments herein. At 302, the method defines one or more non-paresthesia stimulation waveform to be used. The stimulation waveform is defined by one or more parameters forming a therapy parameter set (TPS). Examples of therapy parameters within a TPS include, but are not limited to pulse amplitude, pulse width, interpulse delay, number of pulses per burst, pulse frequency, burst frequency, etc. The TPS is defined such that the stimulation waveform is configured to excite at least one of A-delta fibers and/or C-fibers at the target position. The TPS causes the stimulation waveform to exhibit a morphology that does not excite A-beta fibers at all or sufficiently to induce notable paresthesia, also referred to as a non-A-beta fiber excitation morphology.

At 304, the method senses SAP baseline signals by collecting SAP signals, for a data collection window while no external input is applied to the patient. The SAP baseline signals are indicative of the sensory action potential experienced naturally or inherently by nervous tissue of interest at the target position. The SAP baseline signals, collected over a single data collection window, represent an SAP baseline sample for a single time interval, where the SAP baseline sample is indicative of a baseline responsiveness of the fibers of interest (C-fibers and/or A-delta fibers), such as when no external sensory stimulation is delivered. For example, the baseline responsiveness may correspond to an absence of external pitch, pressure, external temperature source, or any other external input that would otherwise cause activity within the fibers of interest.

Throughout the embodiments described herein, the same electrodes may be used for sensing and stimulation. Alternatively, one group of electrodes may be used for sensing, while a different group of electrodes are used for stimulation. For example, the sensing electrodes may be spaced apart along the lead from the stimulation electrodes. Optionally, the sensing electrodes may be provided on a separate lead unique and distinct from the lead that includes the stimulation electrodes. For example, a conventional SCS lead may be positioned along the spinal column at a desired location in order to deliver therapy at one or more stimulation sites of interest, while a separate sensing lead is provided. As one example, electrodes proximate the dorsal column may be used for stimulation, while separate electrodes proximate the dorsal root ganglion (DRG) or dorsal root (DR) are used for sensing. As a further option, sensing electrodes may be located remote from the DRG or DR, such as within the torso of the body and/or along the extremities of the patient, such as within the arms and legs. Optionally, the burst stimulation waveform may be delivered at electrodes proximate both of the dorsal column and the DRG, while sensing is performed at the DRG or DR.

In various embodiments herein, conventional SCS electrodes and leads may be used for stimulation and/or sensing, provided that the SCS electrodes are configured to be located at a desired proximity relative to a target site or nervous tissue of interest. Additionally or alternatively, the lead to be used for sensing may include micro electrodes (alone or in combination with conventional SCS electrodes), where the micro electrodes that are configured to be placed immediately adjacent fibers of interest, such as C-fibers and/or A-delta fibers.

At 306, the SAP baseline sample is analyzed to define baseline features within the morphology of the SAP signal. For example, the baseline features may represent the frequency of SAP within a certain period of time window, an amplitude of peaks, a number of peaks, a number of direction changes and the like within the SAP baseline sample over the data collection window. The SAP baseline sample (s) and their features described above are stored in memory. The SAP baseline samples may be used over time as a reference for comparison with later collected SAP baseline samples, such as to determine when a patient's inherent level of SAP activity is increasing or decreasing. Optionally, the operations at 304 and 306 may be omitted entirely.

At 308, the method delivers the non-paresthesia stimulation waveform to at least one electrode based on the TPS defined at 302. The stimulation waveform is delivered to at least one stimulation electrode on the lead. The stimulation waveform may represent a series of monophasic pulses (with a positive or negative current pulse) or a series of biphasic waveform (with positive and negative pulses). When the stimulation waveform is biphasic, a first pulse phase may be configured to capture at least a portion of the A-delta fibers and/or C-fibers, while the second pulse phase is configured to repolarize charge at a stimulation site. By repolarizing charge at the stimulation site, the second pulse phase limits an extent of A-delta fiber and/or C-fiber excitation (e.g., a degree to which, or amount of, the fibers of interest are excited).

At 310, the method applies a predetermined external sensory stimulation as a noxious or reference input that is configured to excite the fibers of interest (e.g. A-delta fibers and/or C-fibers). The reference input may represent a predetermined degree or amount of touch, pinch, pressure, application of an external temperature source, or any other noxious external input intended to otherwise cause activity within the fibers of interest. The reference input is applied in a repeatable manner such that a common amount of touch, pinch, pressure, external temperature and the like may be applied repeatedly at different times while SAP signals are collected in connection with different TPS.

At 312, the method senses SAP signals and collects the SAP signals for a data collection window. The SAP signals are indicative of the sensory action potential experienced by nervous tissue of interest at the target position in response to the reference or noxious input. The SAP signals, collected over a single data collection window, represent an SAP sample for a single time interval, where the SAP sample is indicative of a responsiveness of the fibers of interest (C-fibers and/or A-delta fibers) when a predetermined external sensory stimulation is delivered. For example, the responsiveness may correspond to a predetermined amount of touch, pressure, and external temperature source, or any other external input that would otherwise cause activity within the fibers of interest. The SAP signals are saved as an SAP sample.

At 312, the patient also enters a pain score to indicate an amount/degree of pain experienced by the patient relative to a predetermined pain index.

At 314, the method analyzes the SAP signal (e.g., the SAP sample) to obtain activity data associated with the TPS. The activity data corresponds to activity for the fiber of interest, such as at least one of the SAP C-fiber components and/or SAP A-delta fiber components. The analysis at 314 is repeated numerous times to obtain a collection of activity data associated with a group or multiple TPS. In the embodiment illustrated in FIG. 3A, the operation at 314 may be implemented during each iteration through the operation at 308-320. Optionally, the operation at 314 may be implemented once after an entire collection of activity data is obtained from a predetermined number of iterations through the operations at 308-320 for the group or multiple different combinations of therapy parameters.

At 314, the method also saves the pain score, and activity data along with the values for the corresponding therapy parameter set, such as in a memory of the IPG, external programmer or other external device. The activity data, pain scores and the associated therapy parameter set are saved, over time, in connection with delivering therapy based on multiple therapy parameter sets, thereby developing a therapy/sensitivity history for the patient. The therapy/sensitivity history indicates, among other things, a degree to which certain therapies inhibit sensory action potentials along conduction nerve fibers of interest (e.g., the C-fibers and/or A-delta fibers). The sensing and analyzing operations at 310 and 312 are described in more detail in connection with FIG. 3B.

At 316, the method determines whether a sufficient number of SAP samples have been collected (and analyzed). When a sufficient number of SAP samples have been collected, flow moves to 322. When it is determined that additional SAP samples should be collected, flow moves along 318 to 320.

At 320, the method changes a value for one or more of the parameters within the therapy parameter set. The change at 320 may be performed in a predetermined systematic stepwise manner. For example, each parameter within the therapy parameter set may be incrementally adjusted by a select amount during separate iterations through the operations at 308-316. As an example, during iterations 1-3, the method may only change the amplitude of the stimulation waveform between low, medium and high amplitudes, while maintaining constant all other parameters within the TPS. After cycling through each of the pulse amplitudes of interest, the pulse amplitude may be reset to the low level for iterations 4-6, during which the pulse width is changed from short to medium to long. During iterations 7-9, the pulse amplitude may be set to the medium level, while the pulse width is again changed from short to medium to long, while all other parameters are maintained constant. The foregoing process may be repeated until each, or at least a select portion, of the potential permutations and combinations of levels for the parameters are used during the operations at 308-316 to form the group of TPS for which the collection of activity data is accumulated.

Alternatively or additionally, not all permutations and combinations of parameter levels may be used. For example, a physician or other user may select (and/or program) individual TPS of interest to be tested as the group of TPS. For example, the operations at 308-316 may only be repeated for 5 to 10 or 20 different TPS, even though many more permutations and combinations of levels for the various parameters exist. The change performed at 320 may be based on pre-stored settings or may represent an input from a physician or other user during operation.

Optionally, the amount of change during each iteration through 320 may vary, such as with larger step changes made during initial iterations and smaller step changes made during later iterations. Optionally, the amount of change at 320 may be based on a difference between the activity data and the threshold. For example, when the activity data substantially exceeds the threshold, larger changes may be applied to one or more parameters at 320. As the difference between the activity data and threshold decreases, the incremental change in the one or more parameters is changed by similarly/proportionally decreasing amounts. Following 320, flow returns to 308.

The operations at 308-316 build a database, file, or generally a pain-activity data relation corresponding to a relation between high frequency content of the SAP signals and pain scores indicative of a level of pain experienced by the patient.

At 322, the method selects a candidate TPS from the multiple or group of TPS based on one or more criteria of interest. For example, when the criteria of interest represents a threshold or predetermined range for the activity data, the candidate TPS may be selected as the TPS that resulted in activity data that satisfy the threshold or predetermined range. For example, when the criteria of interest represents sensory activity, at 322, the method may identify the SAP sample for which the lowest or smallest amount of activity data was identified. The lowest or smallest amount of activity is measured relative to the activity data of the other SAP samples. The method cross references SAP sample, that exhibits the lowest or smallest amount of activity data, to the corresponding therapy parameter set which is designated as the candidate TPS. As one example, the selection at 322 may seek to optimize the candidate TPS to define as a burst stimulation waveform that affords an SAP activity below a threshold or within a range, collectively referred to as a result of interest, without inducing paresthesia. Once a candidate TPS is selected, the candidate TPS is used for subsequent therapy for a period of time, for example until it becomes desirable to repeat the process of FIG. 3A to determine a new candidate TPS.

The operations at 308-320 may be repeated for a number of different therapy parameter sets. For example, it may be desirable to obtain activity data in connection with 5, 10 or more than 10 different stimulation waveforms, in order to derive a more complete understanding of a particular patient's neural fiber activity respond to different stimulation waveforms. When a sufficient amount of activity data (e.g. enough SAP samples) is collected, the process ends and the candidate TPS is selected and implemented.

The operations at 308-320 are iteratively repeated to form a feedback loop in which the therapy parameter set is continuously updated until obtaining a burst stimulation waveform that inhibits spontaneous action potentials along the slow conduction fibers to no more than a select amount of activity.

FIG. 3B illustrates a process for collecting and analyzing SAP signals to obtain the activity data in connection with the operations 312 and 314 of FIG. 3A in accordance with embodiments herein. The operations of FIG. 3B may be implemented by one or more processors, such as within an implantable pulse generator, and external programmer, an external device and the like. The IPG, external programmer or other external device are coupled to a lead having at least one stimulation electrode that is implanted at a target position proximate to nervous tissue of interest.

At 352, the method utilizes one or more electrodes on one or more leads implanted proximate to the target site to sense SAP signals indicative of a sensory action potential of the nervous tissue of interest. The SAP signals are collected over a data collection window (e.g. a few seconds, a few minutes or otherwise) and saved in memory (e.g., memory 158). The SAP signals are sensed between therapies such that no stimulation is delivered while collecting SAP signals. The electrodes at which the SAP signals are sensed may be the same as, partially common with, or entirely distinct from the electrode or electrodes used to deliver therapy. The electrodes may represent micro-electrodes positioned to directly sense signals from C-fibers. Optionally, the electrodes may represent electrodes on a conventional SCS lead that are positioned and configured to sense sensory action potentials from various fibers within the spinal column, such as the A-beta fibers.

At 354, the method determines whether the SAP signal represents a signal that directly measures the sensory action potential of the conducting fibers of interest, such as C-fibers and/or A-delta fibers. By way of example, when micro electrodes are positioned immediately adjacent C-fibers and/or A-delta fibers, the sensed SAP signal would represent a direct measure of the sensory action potential of the slow conducting fibers of interest. Alternatively, when a conventional lead with larger electrodes are positioned in the dorsal column, the larger electrodes are not positioned immediately adjacent C-fibers and/or A-delta fibers. Instead, the larger electrodes measure a "composite" sensory action potential from multiple types of fibers in the dorsal column, where the composite SAP includes SAP components associated with fast conducting fibers and SAP components associated with slow conducting fibers. For example, the composite SAP signal may include an A-alpha fiber SAP component, A-beta fiber SAP component, an A-delta fiber SAP component, a B-fiber SAP component, a C-fiber SAP component and the like.

At 354, when the method determines whether the sensed SAP signal corresponds directly to the conduction SAP component of interest (e.g. the C-fiber component and/or A-delta fiber component) and thus represents, conduction SAP data of interest, flow moves to 358. Otherwise, when the method determines at 354 that the sensed SAP signal is a composite SAP signal that does not correspond directly to the conduction SAP component of interest, flow moves to 356.

At 356, the method processes the sensed composite SAP signal to identify the conduction SAP component and generates conduction SAP data of interest based thereon. For example, a fast Fourier transform may be applied to the composite SAP signal to separate the frequency components therein. Certain composite frequency components of the sensed composite SAP signal entirely or primarily are generated by conduction nerve fibers of interest (e.g., C-fibers and/or A-delta fibers). Thus, the composite SAP signal may be converted to the frequency domain through an FFT conversion to form FFT converted SAP data. The slow conduction frequency components of interest from the FFT converted SAP data may be isolated, such as through filtering. Next, the conduction frequency components of interest from the FFT converted SAP data may be returned at 358 as conduction SAP data in the frequency domain. Optionally, the conduction frequency components in the frequency domain may be converted through an inverse fast Fourier transform back to the time domain to form conduction SAP data in the time domain.

At 358, the method analyzes the conduction SAP data of interest (in the time domain or frequency domain) for one or more features of interest. For example, the feature of interest may represent a number of positive and negative peaks within the conduction SAP data for a select period of time. When processing the conduction SAP data in the time domain, the operation at 358 may include a binning operation, in which the conduction SAP data is segmented into a series of temporal bins. Each temporal bin may include one or more occurrences of the feature of interest (e.g. spikes or peaks).

At 360, the method counts a number of occurrences of the feature of interest (FOI) within each temporal bin. For example, when analyzing the conduction SAP data in the time domain, each temporal bin may correspond to ½-1 second of conduction SAP data. The conduction SAP data exhibits a number of spikes/peaks within each temporal bin, where the number of spikes/peaks is indicative of, and proportional to, an amount of sensory activity conveyed along the corresponding conduction nervous fibers. As more sensory activity is conveyed along the conduction nervous fibers, the number of spikes/peaks within the temporal bins increase. Conversely, as less sensory activity is conveyed along the conduction nervous fibers, the number of spikes/peaks within the temporal bins decrease.

At 362, the method derives SAP activity level data from the count for the temporal bins. For example, the SAP activity level data may indicate that the number of spikes/peaks are within an acceptable upper limit/range or below an acceptable threshold, thereby indicating that a present therapy is acceptable. Alternatively, the SAP activity level data may indicate that the number of spikes/peaks is not within an acceptable range or exceeds an upper limit/threshold, thereby indicating that the present therapy is not achieving a desired affect and warrants modification. The SAP activity level data is stored in combination with the corresponding therapy. Optionally, additional information regarding the patient's condition may be stored with the SAP activity level data (e.g. heart rate, physical activity level and the like). The SAP activity level data is used in accordance with embodiments herein to adjust the therapy parameter set used to define therapy.

As a further option, the SAP activity level data may give additional information about a nature (e.g., amount and/or direction) of the change in the sensory activity. For example, the SAP activity level data may indicate that the conduction SAP data is exhibiting a certain amount of change (e.g. percentage) in sensory activity (e.g. a 5% increase over the past hour, 10% increase over the past day. The amount of change may be characterized as a "large" or "small" decrease or increase relative to an average level of activity or otherwise. For example, the method may save SAP activity level data over an extended period of time (e.g. several days, several weeks or longer). The SAP activity level data may be averaged or otherwise statistically analyzed to determine a mathematical indicator of certain characteristics of the SAP activity level data. For example, the indicator may denote a baseline amount of sensory activity. The indicator may denote levels of sensory activity associated with known or periodic behavior where such level of reactivity are acceptable and do not warrant modification of the coupled tonic/burst therapy.

The operations of FIG. 3B may be repeated throughout operation periodically based upon inputs from a patient or clinician, periodically based upon an operation of the IPG and the like.

FIG. 3C illustrates a process for generating a correlation between pain scores that are noted down by a patient and features of SAP recorded by the IPG (e.g. counts of SAP in each defined time period of window) in connection with multiple non-paresthesia therapies in accordance with embodiments herein. Initially, an NS system 100 is implanted and non-paresthesia therapy is delivered as explained hereafter, while the patient is requested to provide pain scores in connection with pain intensity experienced by the patient.

At 370, the method delivers a non-paresthesia stimulation waveform (defined by a present therapy parameter set) to at least one electrode.

At 372, the method senses SAP signals and collects the SAP signals for a data collection window. The SAP signals are indicative of the sensory action potential experienced by nerve tissue of interest at the target position with or without noxious input (e.g., due solely to inherent pain). At 372, the patient is also requested to enter a pain intensity score indicative of a level of pain experienced by the patient.

At 374, the method analyzes the SAP signal (e.g., the SAP sample) to obtain SAP activity data associated with the TPS. As explained herein, the analysis of the SAP signal may produce an indication of a high frequency (HF) content within the SAP sample, where the HF content corresponds to electrical activity exhibited by the fibers of interest, such as at least one of the SAP C-fiber components and/or SAP A-delta fiber components.

At 376, the method determines whether a sufficient number of SAP samples have been collected (and analyzed). When a sufficient number of SAP samples have been collected, flow moves to 378. At 378, the method changes a value for one or more of the parameters within the therapy parameter set.

At 376, when it is determined that additional SAP samples should be collected, the process of FIG. 3C ends. The operations at 370-378 may be repeated while changing at least one parameter, thereby defining multiple therapy parameter sets, each set of which is recorded with a corresponding HF content for the SAP signal and patient designated pain score. The process of FIG. 3C generates a patient specific pain-activity data relation (also referred to as a patient specific PAD relation) defining a function or relation between HF content of the SAP signals and pain scores designated by the patient. The patient specific PAD relation may be stored in memory of the NS system 100, an external programmer, another external device, or in a database, on a network, and the like. By way of example, the patient specific PAD relation may be used by an NS system 100 in connection with automatically adjusting therapy parameters without further input from the patient.

FIG. 3D illustrates a process for selecting a non-paresthesia therapy in accordance with embodiments herein. Initially, an external programmer is provided that is used to select therapy parameters to define a non-paresthesia therapy. The external programmer may be used to control the NS system 100 that has been implanted. Alternatively, the external programmer may be coupled to and implanted lead, prior to implant of the NS system 100. Alternatively or additionally, the external programmer may be coupled to a temporary lead not intended for permanent implant.

At 390, the method delivers a non-paresthesia stimulation waveform (defined by a present therapy parameter set) to at least one electrode, either coupled to the external programmer or coupled to the NS system 100, under control of the external programmer.

At 392, the method senses SAP signals and collects the SAP signals for a data collection window. At 392, the method analyzes the SAP signal (e.g., the SAP sample) to obtain SAP activity data, such as the HF content of the A-delta fiber component and/or C-fiber component of the SAP signal.

At 394, the method determines whether the activity data that apply a criteria of interest. For example, the method may determine whether the high frequency content of the SAP signal falls below a threshold or within an acceptable range, thereby indicating that no pain or an acceptable low level of pain is experienced by the patient in connection with the present therapy parameter set. As one example, the threshold may represent a predetermined HF content level set by a physician, alone or in combination with feedback from the patient.

Alternatively or in addition, the threshold may be set based on the patient specific PAD relation. For example, at 394, the method may access the patient specific PAD relation corresponding to the present patient and uses the patient specific PAD relation to determine a range or threshold for HF content, at which a patient experience no pain or an acceptable low level of pain. At 394, the method may compare the HF content identified at 392 to the patient specific PAD relation, to obtain a corresponding pain score. When the corresponding pain score associated with the measured HF content is below a pain threshold or within an acceptable pain range, at 394 the method may determine that the HF content of the SAP signal is acceptable and that the present therapy parameter set should be utilized long-term. Thus, flow moves to 398 and the process ends.

Alternatively, at 394, when the method determines that the high frequency content of the SAP signal exceeds a threshold or acceptable range, flow moves to 396. At 396, the method changes one or more therapy parameters and flow returns to 390, at which a new non-paresthesia therapy is delivered in accordance with the new therapy parameters.

The operation at 390-398 are iteratively repeated until the high frequency content of the measured SAP signal indicates that the present non-paresthesia therapy will sufficiently suppressed pain experienced by the patient. Optionally, the operations at 390-398 may be repeated a predetermined number of times, after which the process terminates and a one of the non-paresthesia therapies is selected that resulted in a desired change in the SAP signal (e.g. the lowest high frequency content).

FIGS. 5A-5D illustrate examples of sensory action potential signals collected in accordance with embodiments herein. In FIGS. 5A-5D, the vertical axis corresponding to the measured voltage potential, and the horizontal axis corresponding to time. FIGS. 5A-5D illustrate examples of potential SAP signals 502, 504, 506 and 508 that may be collected in connection with delivery of burst stimulation waveforms defined by different therapy parameter sets. The SAP signals 502-508 include SAP sample windows separated by therapy delivery windows. With respect to the SAP signal 502, first and second SAP sample windows 510, 514 are illustrated to be separated by a burst therapy delivery window 528. When SAP signal 502 is collected in the SAP sample windows 510 and 514, no therapy is delivered. When the burst therapy is delivered during the therapy delivery window 528, the SAP signal 502 is not collected. Similarly, the SAP signals 504-508 include SAP sample windows 516-526, and therapy delivery windows 530-534. The SAP signal is collected in such a way due to the pacing spike from IPG overlapping with SAP signals in time windows 528, 530, 532 and 534, and the adjacent following SAP signals are taken as the SAP associated with each burst stimulation setting in order to be able to analyze the high component of SAP signals, rather than pacing spikes.

In another embodiment, when the pacing spike or artifact from the IPG is blanked appropriately so that no stimulation spike could interrupt the counting of SAP, the SAP signals can be collected for two or more time periods in collection windows with and without burst stimulation.

The burst stimulation waveform included fixed parameters of 7 pulses/burst, pulse frequency of 500 Hz, burst frequency of 40 Hz and an amplitude of 90% of the motor threshold for all of SAP signals 502-508. In connection with the SAP signal 502, the burst stimulation waveform was delivered during the therapy delivery window 528, wherein a pulse width of 250 μs is used (as one of the therapy parameters) for each pulse. In connection with the SAP signal 504, a pulse width of 500 μs was used for each pulse of the burst stimulation waveform delivered during the burst therapy delivery window 530. Pulse widths of 750 μs and 1000 μs were used for the burst stimulation waveforms delivered during the burst therapy delivery windows 532 and 534, respectively, in connection with SAP signals 506 and 508.

Before, during an initial portion, or throughout data collection during the SAP sample windows 510, 514, a reference noxious input is applied to one or more predetermined areas of the patient. For example, the patient may be pinched, have a hot/cold source applied, scratched or otherwise receive an external input intended to evoke a sensory response. The reference noxious input may be applied to one or more areas on one or more limbs of the patient.

FIGS. 5A-5D also illustrate SAP activity data 540-546 that is obtained when the SAP signals 502-508, respectively, are analyzed. The activity data 540-546 is divided into activity data segments 548-562. For example, the activity data 540 includes first and second SAP activity data segments 548 and 550. The first activity data segment 548 may also be referred to as a pre-therapy SAP activity data segment 548, as the SAP sample window 510 occurs before delivery of the burst stimulation waveform during window 528. The second activity data segment 550 may also be referred to as a post therapy activity data segment 550, as the SAP sample window 514 occurs after delivery the burst stimulation waveform during window 528. The activity data 542-546 are also partitioned into pre-therapy activity data segments 552, 556 and 560, and post therapy activity data segments 554, 558 and 562.

The pre- and post-therapy SAP activity data segments 548-562 are divided into temporal bins 568, each bin of which corresponds to a temporal portion of the SAP signals 502-508. The data segments 548-562 include counts 564 of the number of peaks or spikes in the corresponding SAP signal 502-508 for the corresponding temporal bin 568. The counts 564 correspond to the number of neuronal firing evoked by the noxious input (e.g., a pinch of a forearm).

The data segments 552, 556 and 560 exhibit high counts 564 within a majority of the bins 568, as compared to the data segments 554, 558 and 562 which exhibit lower count 564 within a majority of the bins 568. The frequency/count 564 may be summed for each single data segment 548-562 and compared to the related data segment (e.g., data segment 548 compared to 550) to determine a change in activity. By way of example, the sum of the count 564 of spikes in the post therapy data segment 554 (corresponding to the SAP sample window 518) exhibits a 15% decrease in the count of spikes, as compared to the sum of the count of spikes in the pre-therapy data segment 552 (corresponding to the SAP sample window 516). The sum of the count 564 of spikes in the post therapy data segment 558 (corresponding to the SAP sample window 522) exhibits a 24% decrease in the count of spikes, as compared to the sum of the count of spikes in the pre-therapy data segment 556 (corresponding to the SAP sample window 520). The sum of the count 564 of spikes in the post therapy data segment 562 (corresponding to the SAP sample window 526) exhibits a 49% decrease in the count of spikes, as compared to the sum of the count of spikes in the pre-therapy data segment 560 (corresponding to the SAP sample window 524).

When the counts 564 in the activity data segments 552, 556 and 560 are compared to the counts 564 in the activity data segments 554, 558 and 562, it is seen that the sensory action potential (as measured in the SAP signals 504-508) was reduced/attenuated after delivery of the burst stimulation waveforms to varying degrees. The degree to which the sensory action potential was attenuated is dependent, at least in part, on the burst therapy parameters. When no burst stimulation waveforms are delivered, the frequency content of the sensory action potential measured over the A-delta and C-fibers is higher. After delivery of a burst stimulation waveform, the sensory action potentials are suppressed and the frequency content of SAP decreased. As explained herein, methods and systems are provided to determine and control therapy parameter sets for burst and/or high frequency stimulation waveforms based on closed loop sensory measurement.

Figure 6:
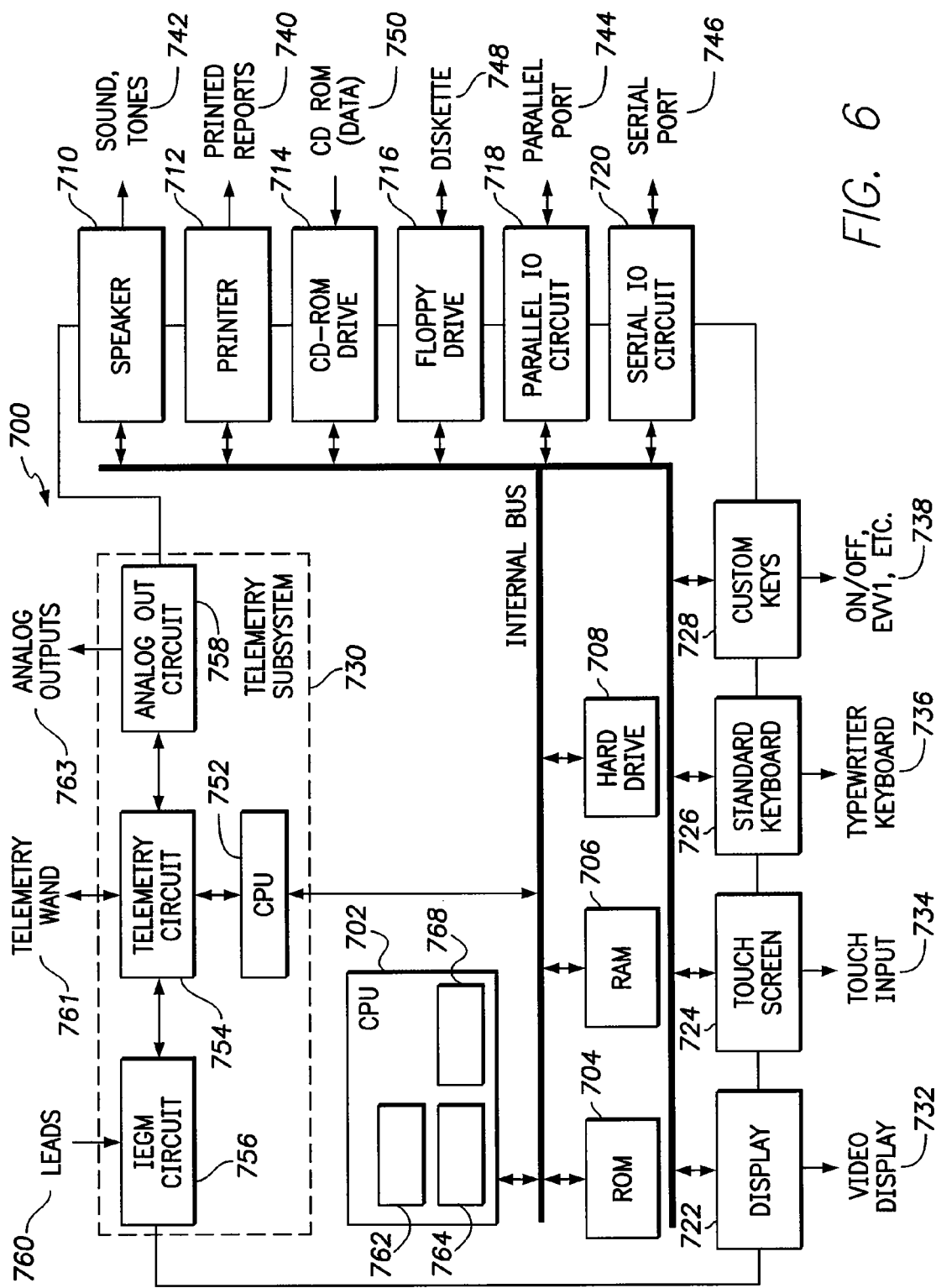
FIG. 6 illustrates a functional block diagram of an embodiment of an electronic control unit that is operated in accordance with the processes described herein.

FIG. 6 illustrates a functional block diagram of an embodiment of an electronic control unit (ECU) 700 that is operated in accordance with the processes described herein to analyze SAP signals and to interface with one or more IPGs and/or leads with electrodes positioned at stimulation sites to deliver coupled tonic/burst therapies and/or sense sensory action potential signals. The ECU 700 may be a workstation, a portable computer, a PDA, a cell phone and the like. The ECU 700 includes an internal bus that connects/interfaces with a Central Processing Unit (CPU) 702, ROM 704, RAM 706, a hard drive 708, the speaker 710, a printer 712, a CD-ROM drive 714, a floppy drive 716, a parallel I/O circuit 718, a serial I/O circuit 720, the display 722, a touch screen 724, a standard keyboard connection 726, custom keys 728, and a telemetry subsystem 730. The internal bus is an address/data bus that transfers information between the various components described herein. The hard drive 708 may store operational programs as well as data, such as waveform templates and detection thresholds.

The CPU 702 typically includes a microprocessor, a microcontroller, or equivalent control circuitry, and may interface with an IPG and/or lead. The CPU 702 may include RAM or ROM memory, logic and timing circuitry, state machine circuitry, and I/O circuitry to interface with the IPG and/or lead. The display 722 (e.g., may be connected to the video display 732). The touch screen 724 may display graphic information relating to the CNS 110. The display 722 displays various information related to the processes described herein. The touch screen 724 accepts a user's touch input 734 when selections are made. The keyboard 726 (e.g., a typewriter keyboard 736) allows the user to enter data to the displayed fields, as well as interface with the telemetry subsystem 730. Furthermore, custom keys 728 turn on/off 738 (e.g., EVVI) the ECU 700. The printer 712 prints copies of reports 740 for a physician to review or to be placed in a patient file, and speaker 710 provides an audible warning (e.g., sounds and tones 742) to the user. The parallel I/O circuit 718 interfaces with a parallel port 744. The serial I/O circuit 720 interfaces with a serial port 746. The floppy drive 716 accepts diskettes 748. Optionally, the floppy drive 716 may include a USB port or other interface capable of communicating with a USB device such as a memory stick. The CD-ROM drive 714 accepts CD ROMs 750.

The CPU 702 is configured to analyze SAP signals collected by one or more electrodes. The CPU 702 includes a therapy circuit module 764 that is configured to control delivery of a first current pulse configured as a tonic stimulation waveform to the at least one electrode. The tonic stimulation waveform is configured to excite A-beta fibers of the nervous tissue. The therapy circuit module 764 is further configured to, after a tonic-burst delay, control delivery of second current pulses configured as a burst stimulation waveform to at least one electrode. The burst stimulation waveform is configured to excite C-fibers of the nervous tissue.

The CPU 702 also includes a delay adjustment circuit module 762 that adjusts the tonic-burst delay between the tonic and burst stimulation waveforms to deliver the burst stimulation waveform during a refractory period of the A-beta fibers excited by the tonic stimulation waveform to avoid excitation of the A-beta fibers excited by the tonic stimulation waveform, as explained herein. For example, the delay adjustment circuit module 762 may adjust the tonic-burst delay to reduce the C-fiber SAP component The CPU 702 also includes an SAP analysis circuit module 768 that receives sensed SAP signals from at least one electrode on the lead, and analyzes the SAP signals to identify a C-fiber sensory action potential (C-fiber SAP) component of the signals. For example, the SAP analysis circuit module 768 may determine an amount to adjust the tonic-burst delay based on the C-fiber SAP component of the signals. The SAP analysis circuit module 768 may adjust analyze a feature of interest from a morphology of the C-fiber SAP component over time, count a number of occurrences of the feature of interest that occur within the C-fiber SAP component over a predetermined duration, compare the number of occurrences to a prior number of occurrences, and determine and amount to adjust the tonic-burst delay based on the comparing operation. The SAP analysis circuit module 768 may analyze the C-fiber SAP component to determine SAP activity level data for a present/current coupled tonic/burst therapy. The SAP activity level data is saved in memory with the associated therapy parameters.

In accordance with at least one embodiment, SAP activity level data is collected in connection with a plurality of coupled tonic-burst therapies. The SAP activity levels are compared and a select one of the SAP activity levels is chosen. For example, a lowest SAP activity level may be chosen. Alternatively, a most frequent SAP activity level may be chosen. Alternatively, a lowest or most frequent SAP activity level within a select range or below an upper limit may be chosen. A coupled tonic-burst therapy associated with the chosen SAP activity level is identified from the therapies stored in memory. The delay adjustment circuit module 762 adjusts the tonic-burst delay to correspond to the identified coupled tonic-burst therapy.

The telemetry subsystem 730 includes a central processing unit (CPU) 752 in electrical communication with a telemetry circuit 754, which communicates with both an SAP circuit 756 and an analog out circuit 758. The circuit 756 may be connected to leads 760. The circuit 756 may also be connected to implantable leads to receive and process SAP signals. Optionally, the SAP signals sensed by the leads may be collected by the CNS 110 and then transmitted, to the ECU 700, wirelessly to the telemetry subsystem 730 input.

The telemetry circuit 754 is connected to a telemetry wand 761. The analog out circuit 758 includes communication circuits to communicate with analog outputs 763. The ECU 700 may wirelessly communicate with the CNS 110 and utilize protocols, such as Bluetooth, GSM, infrared wireless LANs, HIPERLAN, 3G, satellite, as well as circuit and packet data protocols, and the like. Alternatively, a hard-wired connection may be used to connect the ECU 700 to the CNS 110.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) are hardwired to perform the methods or portions of the methods described herein, and/or when the processors (e.g., of the devices described herein) operate according to one or more software programs that are written by one or more persons of ordinary skill in the art to perform the operations described in connection with the methods.

The controller 160 may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. Additionally or alternatively, the controllers 151, 206, 1006 and the controller device 160 may represent circuit modules that may be implemented as hardware with associated instructions (for example, software stored on a tangible and non-transitory computer readable storage medium, such as a computer hard drive, ROM, RAM, or the like) that perform the operations described herein. The above examples are exemplary only, and are thus not intended to limit in any way the definition and/or meaning of the term "controller." The controllers and the controller device may execute a set of instructions that are stored in one or more storage elements, in order to process data. The storage elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. §112(f), unless and until such claim limitations expressly use the phrase "means for" followed by a statement of function void of further structure.

What is claimed is:

1. A method to treat chronic pain in a patient by controlling non-paresthesia stimulation of nervous tissue of a spinal cord of the patient, the method comprising:
providing a lead having at least one electrode on the lead configured to be implanted at a target position with an epidural space and proximate to nervous tissue of the spinal cord of the patient;
delivering a non-paresthesia stimulation waveform to the at least one electrode based on a therapy parameter set (TPS), the stimulation waveform including a series of pulses configured to excite at least one of A-delta fibers or C-fibers of the nervous tissue of the spinal cord of the patient;
sensing sensory action potential (SAP) signals;
iteratively repeating the delivering and sensing operations while changing at least one parameter from the TPS;
analyzing the SAP signals to obtain SAP activity data associated with the TPS for at least one of an SAP C-fiber component or an SAP A-delta fiber component, the analyzing operations obtaining a collection of SAP activity data associated with multiple therapy parameter set;
selecting one or more parameters for the TPS based on the collection of SAP activity data;
programming an implantable pulse generator to deliver stimulation to nervous tissue of the spinal cord according to the TPS; and
activating the implantable pulse generator to deliver electrical stimulation to the patient according to the programmed TPS.

2. The method of claim 1, further comprising selecting a candidate TPS from the multiple therapy parameter set, wherein the candidate TPS selected has corresponding SAP activity data that meets a criteria of interest.

3. The method of claim 2, wherein the selecting operation includes optimizing the candidate TPS to a stimulation configuration that affords a result of interest without inducing paresthesia.

4. The method of claim 1, wherein the analyzing operation identifies a high frequency content of at least one of the SAP C-fiber component or the A-delta fiber component within the SAP signals sensed.

5. The method of claim 1, further comprising applying a reference noxious input during an interval between successive burst waveforms, the reference noxious input creating the SAP signals sensed.

6. The method of claim 1, further comprising changing at least one of the parameters for the TPS during each iteration through the delivering, sensing and analyzing operation.

7. The method of claim 1, wherein the criteria of interest represents a number of peaks that occur in the SAP signal and the candidate TPS selected has a fewest number of peaks with respect to the multiple therapy parameter sets analyzed.

8. The method of claim 1, wherein the therapy parameters define at least one of a burst stimulation waveform or a high frequency stimulation waveform.

9. A system to treat chronic pain in a patient by controlling non-paresthesia stimulation of nervous tissue of a spinal cord of the patient, the system comprising:
a lead having at least one stimulation electrode, the lead configured to be implanted at a target position within an epidural space proximate to nervous tissue of the spinal cord; and
an implantable puke generator (IPG) coupled to the lead, the IPG configured to:
deliver a stimulation waveform to the at least one electrode based on a therapy parameter set (TPS), the stimulation waveform including a series of pulses configured to excite at least one of a-Delta fibers or C-fibers of the nervous tissue of the spinal cord;
sense sensory action potential (SAP) signals;
iteratively repeat the delivering and sensing operations while changing at least one parameter from the TPS;
analyze the SAP signals to obtain SAP activity data associated with the TPS for at least one of an SAP C-fiber component or an SAP A-delta fiber component, the analyzing operations obtaining a collection of SAP activity data associated with multiple therapy parameter sets (TPSs);
select one or more parameters for the TPS based on the collection of SAP activity data;
provide non-paresthesia electrical stimulation to the patient according to the TPS selected based on the collection of SAP activity data.

10. The system of claim 9, wherein the processor is configured to select a candidate TPS from the multiple therapy parameter sets based on a criteria of interest related to the SAP activity data, and utilize the candidate TPS in connection with delivering non-paresthesia therapy.

11. The system of claim 9, further comprising memory configured to store a pain-SAP activity data relation defining a relation between high frequency content of the SAP signals and pain scores indicative of pain experienced by a patient.

12. The system of claim 9, wherein the at least one electrode includes a microelectrode configured to be located immediately adjacent C-fibers and configured to sense a C-fiber sensory action potential (SAP) directly at the microelectrode.

13. The system of claim 9, wherein the processor is configured to receive a pain score indicative of a level of pain experienced by the patient in connection with each of the therapy parameter sets, the processor configured to define a relation between the SAP activity data and the pain scores and save the relation in memory.

14. The system of claim 9, wherein the therapy parameters define at least one of a burst stimulation waveform or a high frequency stimulation waveform.

* * * * *